(12) United States Patent
Kitawaki et al.

(10) Patent No.: US 7,691,255 B2
(45) Date of Patent: Apr. 6, 2010

(54) SENSOR, MEASURING DEVICE, AND MEASURING METHOD

(75) Inventors: Fumihisa Kitawaki, Ehime (JP); Akihito Kamei, Kyoto (JP); Tatsurou Kawamura, Kyoto (JP)

(73) Assignee: Panasonic Corporation, Osaka (JP)

( * ) Notice: Subject to any disclaimer, the term of this patent is extended or adjusted under 35 U.S.C. 154(b) by 777 days.

(21) Appl. No.: 11/579,638

(22) PCT Filed: Apr. 22, 2005

(86) PCT No.: PCT/JP2005/007727

§ 371 (c)(1),
(2), (4) Date: Nov. 6, 2006

(87) PCT Pub. No.: WO2005/188960

PCT Pub. Date: Nov. 17, 2005

(65) Prior Publication Data

US 2008/0105566 A1    May 8, 2008

(30) Foreign Application Priority Data

May 6, 2004  (JP) .............................. 2004-137075

(51) Int. Cl.
*G01N 27/327* (2006.01)
*G01N 27/333* (2006.01)
*G01N 21/00* (2006.01)

(52) U.S. Cl. ...................... 205/777.5; 206/789; 422/58; 422/57

(58) Field of Classification Search ..............................
204/403.01–403.15, 416; 205/777.5, 778, 205/792, 789; 422/55–58
See application file for complete search history.

(56) References Cited

U.S. PATENT DOCUMENTS 4,340,564 A * 7/1982 Harte et al. .................... 422/56
4,676,653 A * 6/1987 Strohmeier et al. ......... 356/446

(Continued)

FOREIGN PATENT DOCUMENTS

EP        0 545 284 A     6/1993

(Continued)

OTHER PUBLICATIONS

European Search Report issued in European Patent Application No. EP 05 73 4708 dated Feb. 17, 2009.

*Primary Examiner*—Alex Noguerola
(74) *Attorney, Agent, or Firm*—McDermott Will & Emery LLP

(57) ABSTRACT

A sensor capable of measuring a plurality of measuring items quickly and accurately, a measuring device, and a measuring method are provided. The sensor includes a sample-holding unit for holding a sample containing an analyte; a sample-supplying port for supplying the sample to the sample-holding unit; a detecting unit for carrying out an electrochemical measurement, the unit being provided in the sample-holding unit; an optical measuring unit for carrying out an optical measurement, the unit being provided in the sample-holding unit; and a reagent-holding unit for holding a reagent for the optical measurement, the unit being provided in the sample-holding unit; wherein in the flowing direction of the sample supplied from the sample-supplying port in sample-holding unit, the sample-supplying port, the detecting unit, and the reagent-holding unit are positioned in the order recited.

3 Claims, 14 Drawing Sheets

U.S. PATENT DOCUMENTS

| | | | |
|---|---|---|---|
| 4,867,946 A * | 9/1989 | Gross et al. | 422/82.09 |
| 5,059,394 A * | 10/1991 | Phillips et al. | 422/68.1 |
| 5,141,868 A | 8/1992 | Shanks et al. | |
| 5,208,147 A * | 5/1993 | Kagenow et al. | 435/14 |
| 6,340,428 B1 | 1/2002 | Ikeda et al. | |
| 6,670,192 B1 | 12/2003 | Galen et al. | |
| 2004/0043477 A1 | 3/2004 | Schibli | |

FOREIGN PATENT DOCUMENTS

| | | |
|---|---|---|
| JP | 60-052761 | 3/1985 |
| JP | 03-046566 | 2/1991 |
| JP | 07-248310 | 9/1995 |
| JP | 9-503581 | 4/1997 |
| JP | 09-127126 | 5/1997 |
| WO | WO 95/06240 | 3/1995 |

* cited by examiner

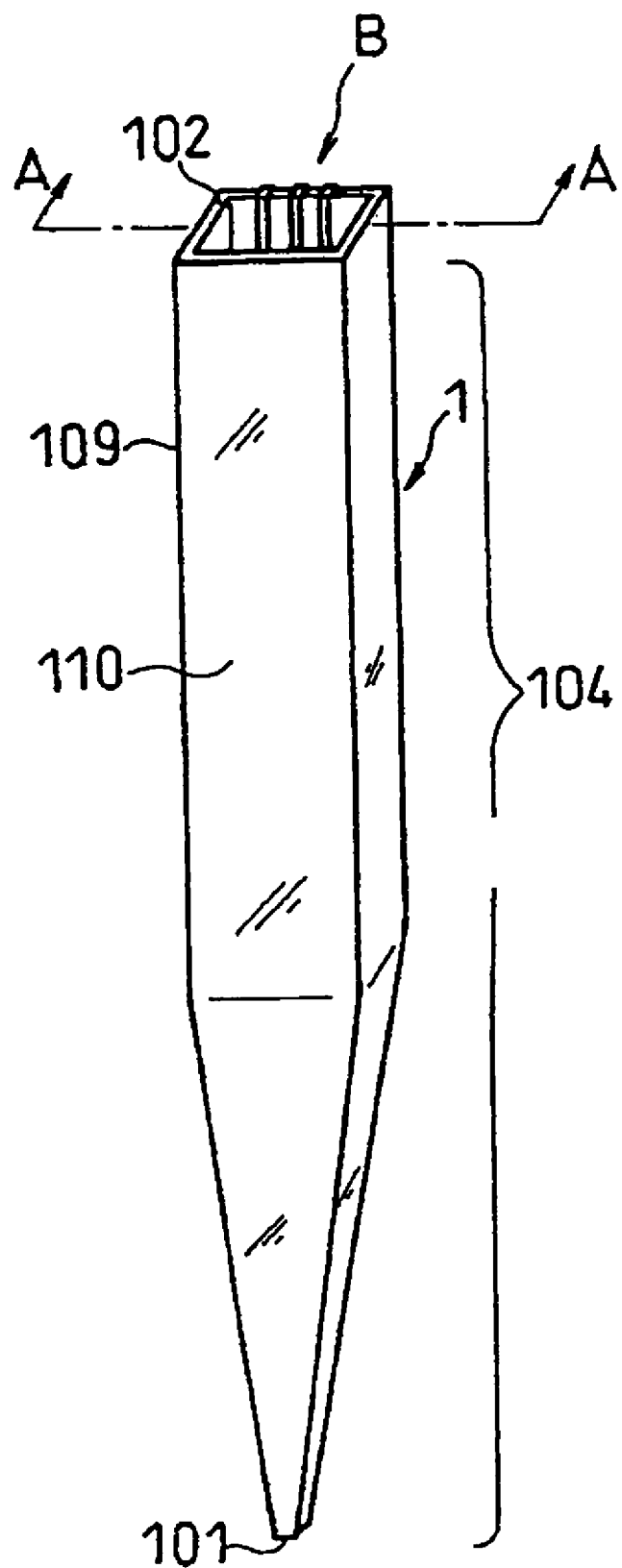
[FIG.1]

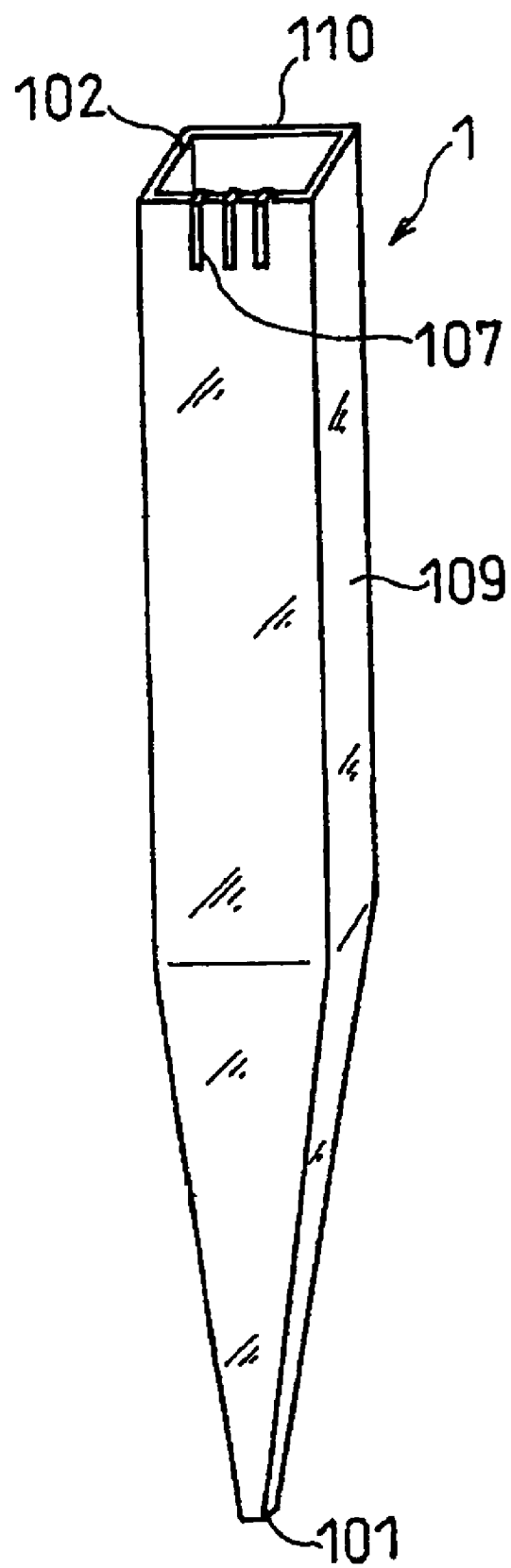
[FIG.2]

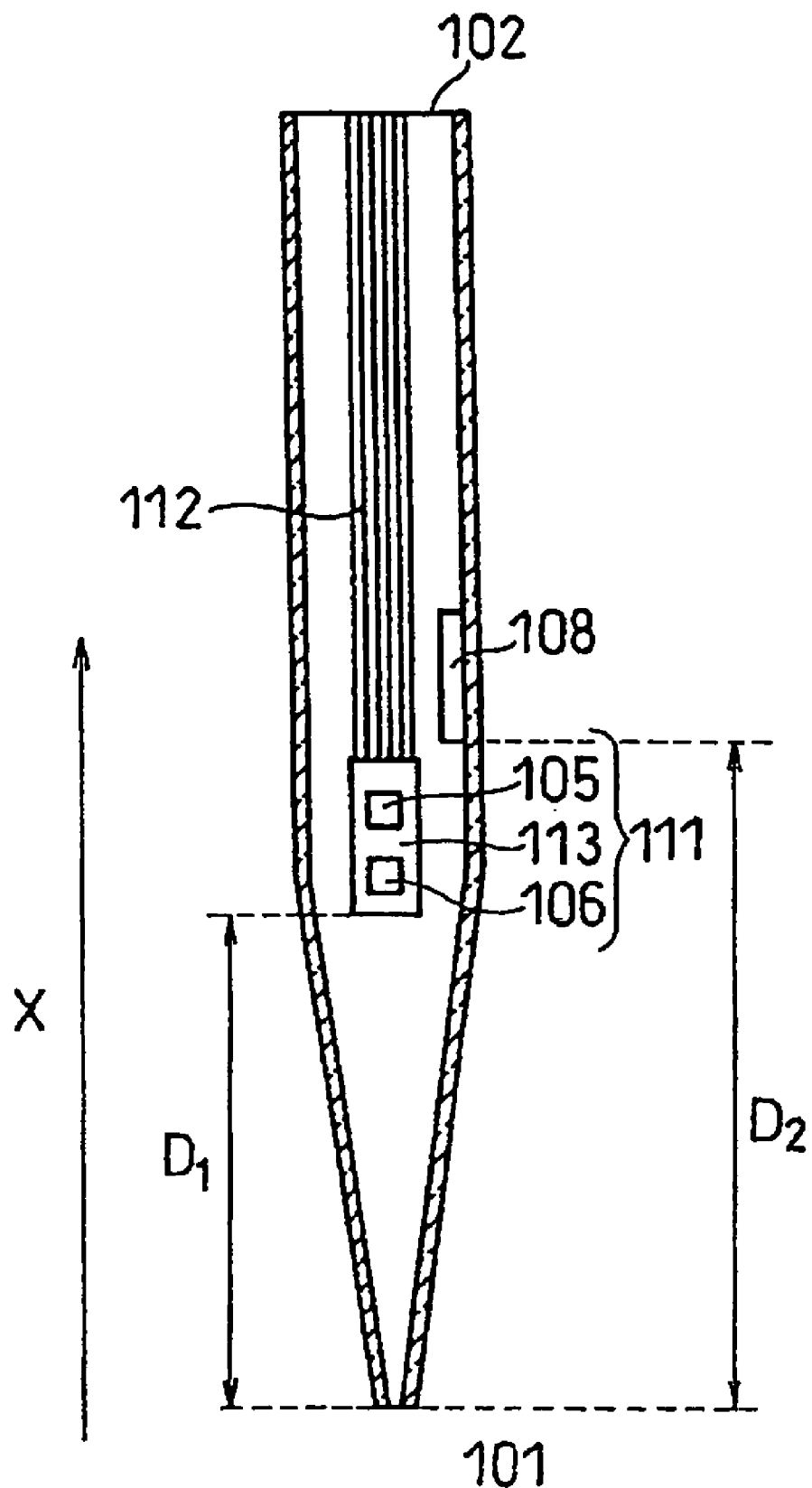
[FIG.3]

[FIG. 4]
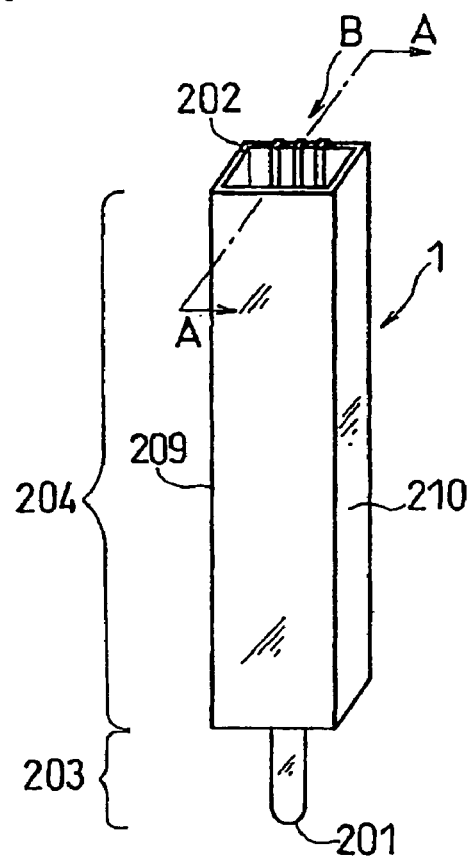
[FIG. 5]
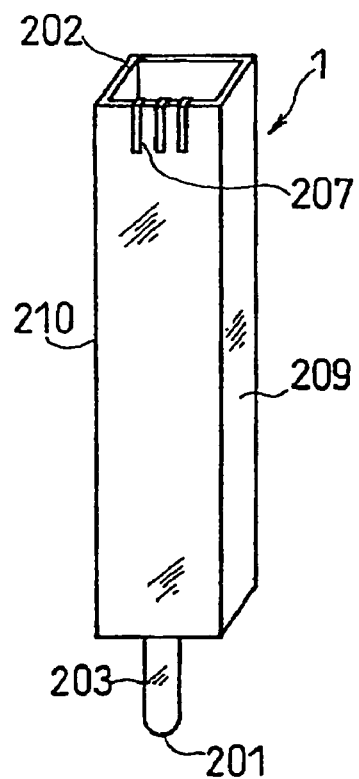

[FIG.6]
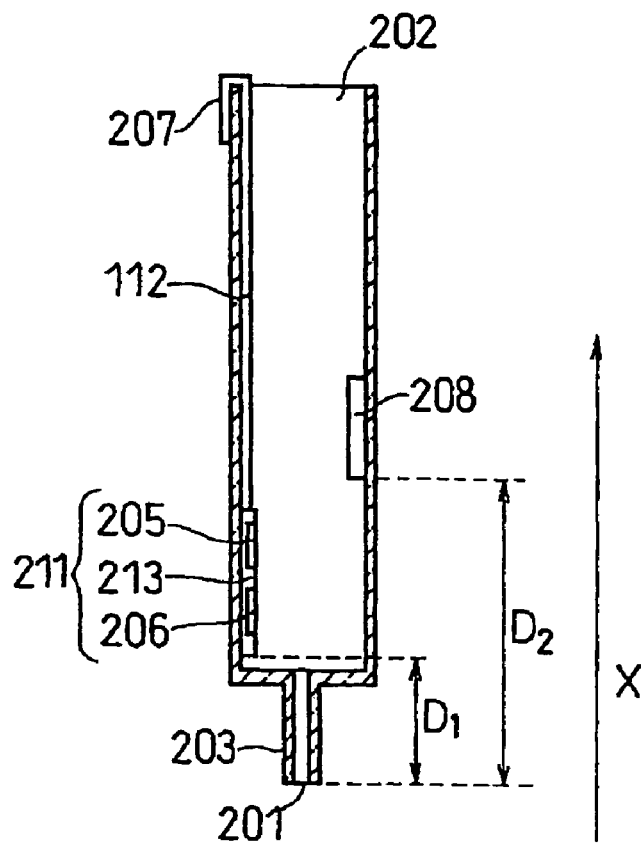
[FIG.7]
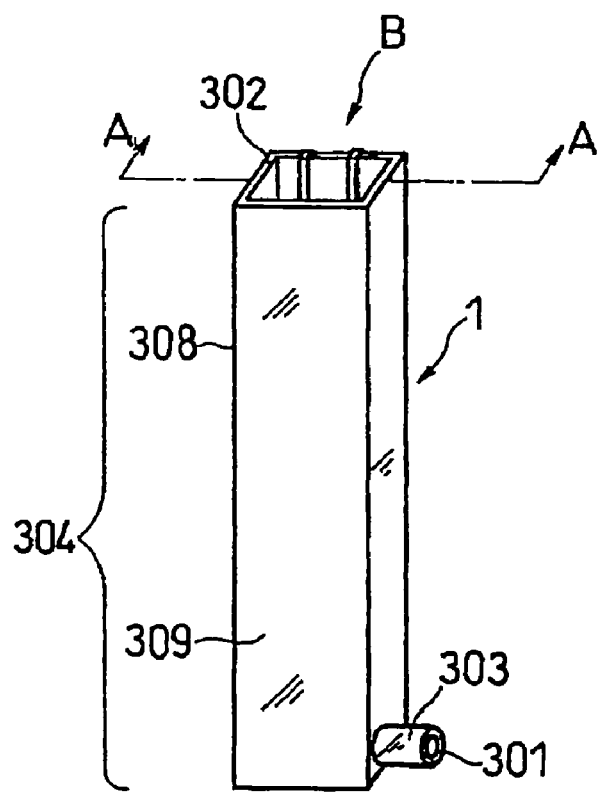

[FIG. 8]
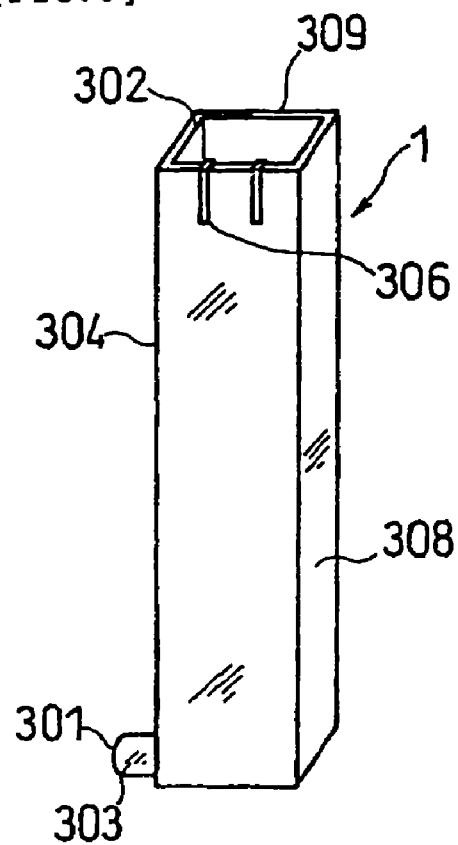
[FIG. 9]
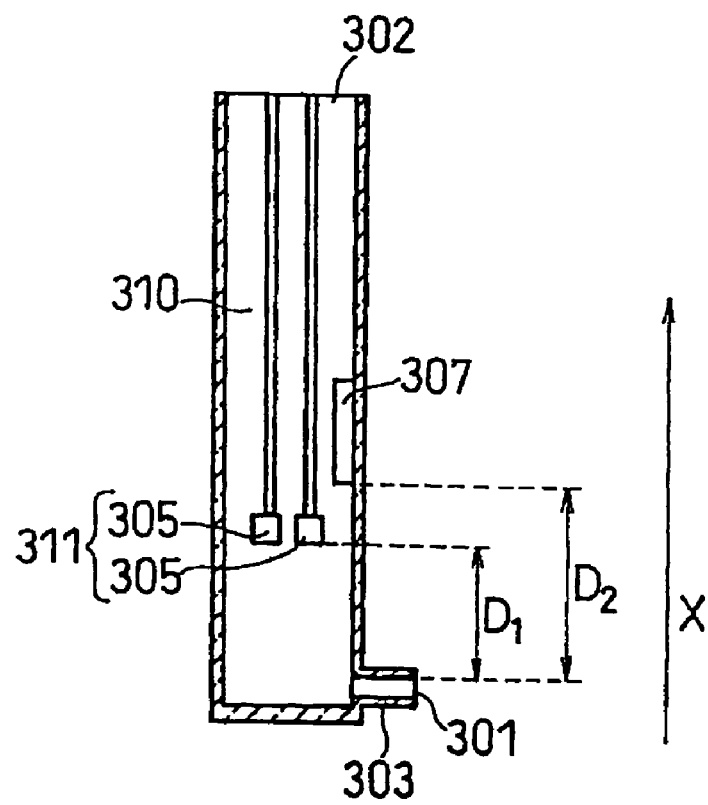

[FIG.10]
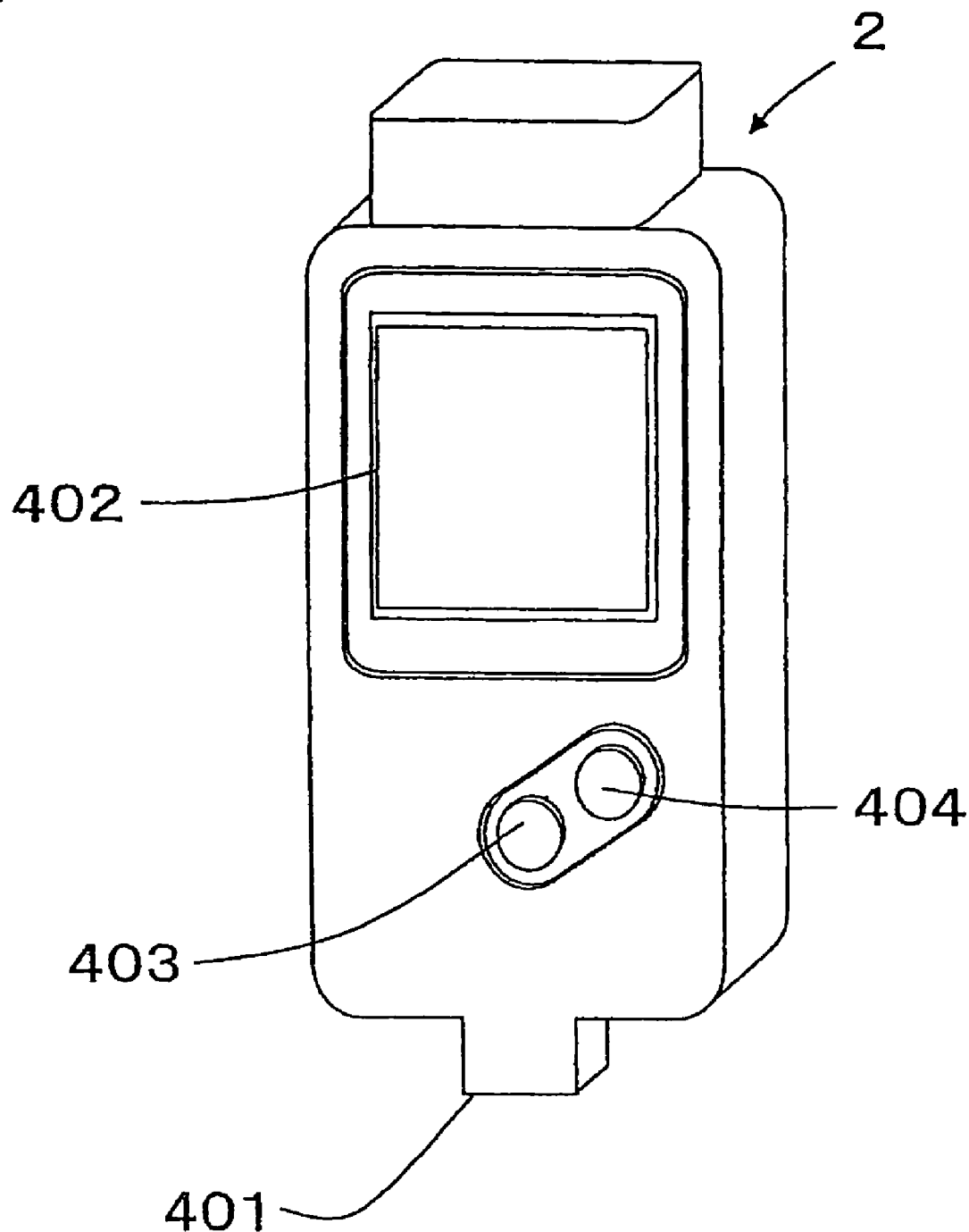

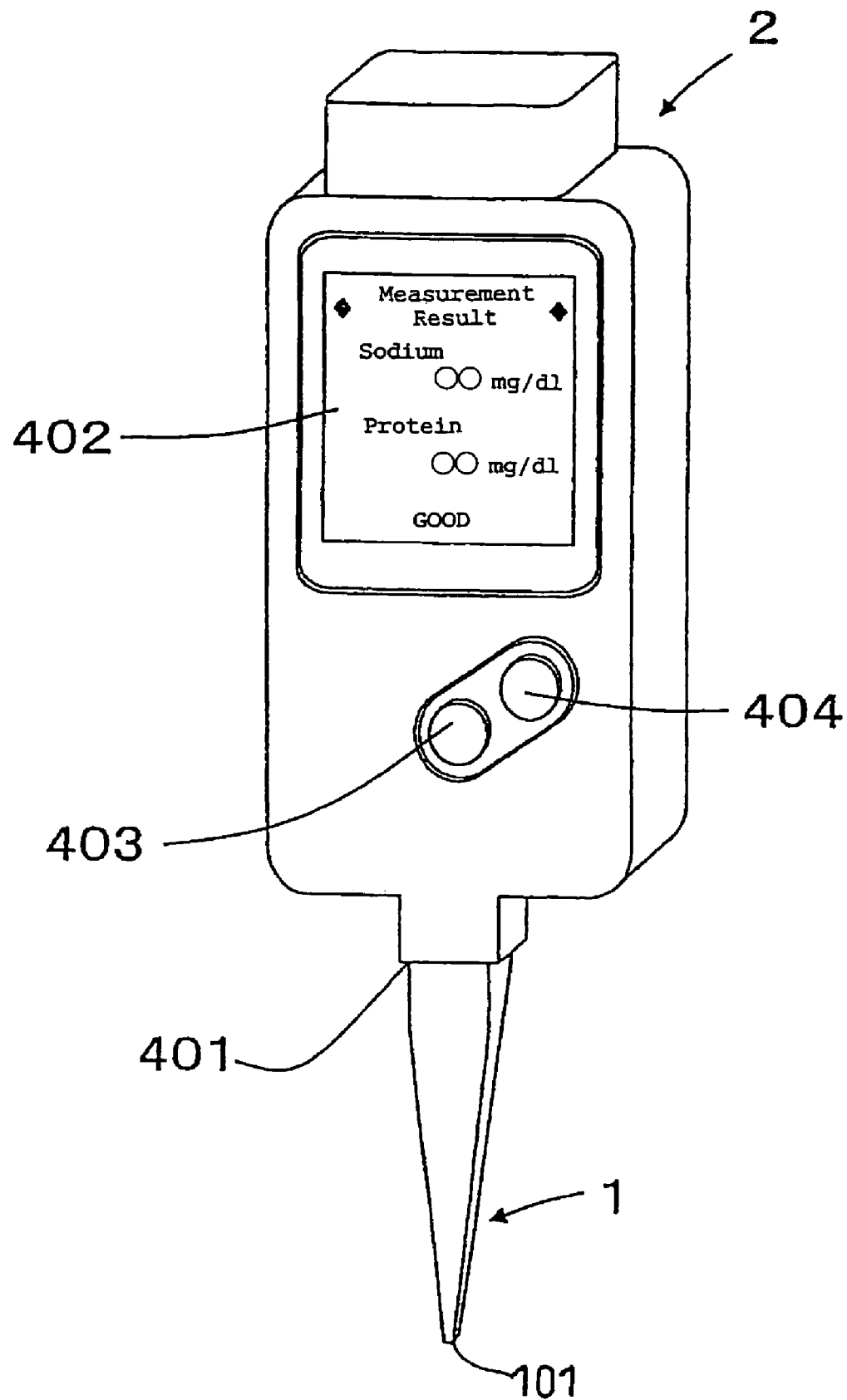
[FIG.11]

[FIG.12]
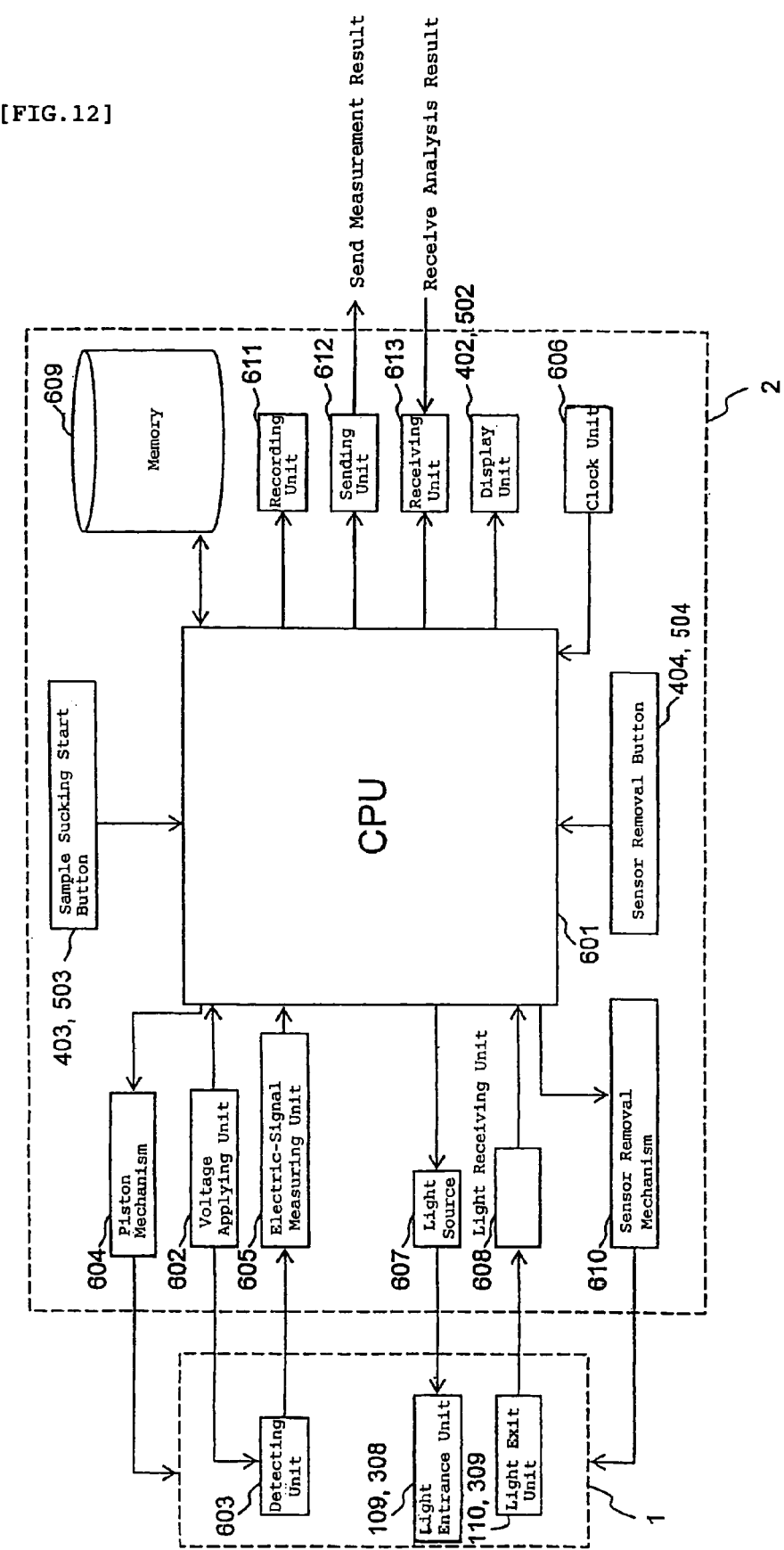

[FIG.13]
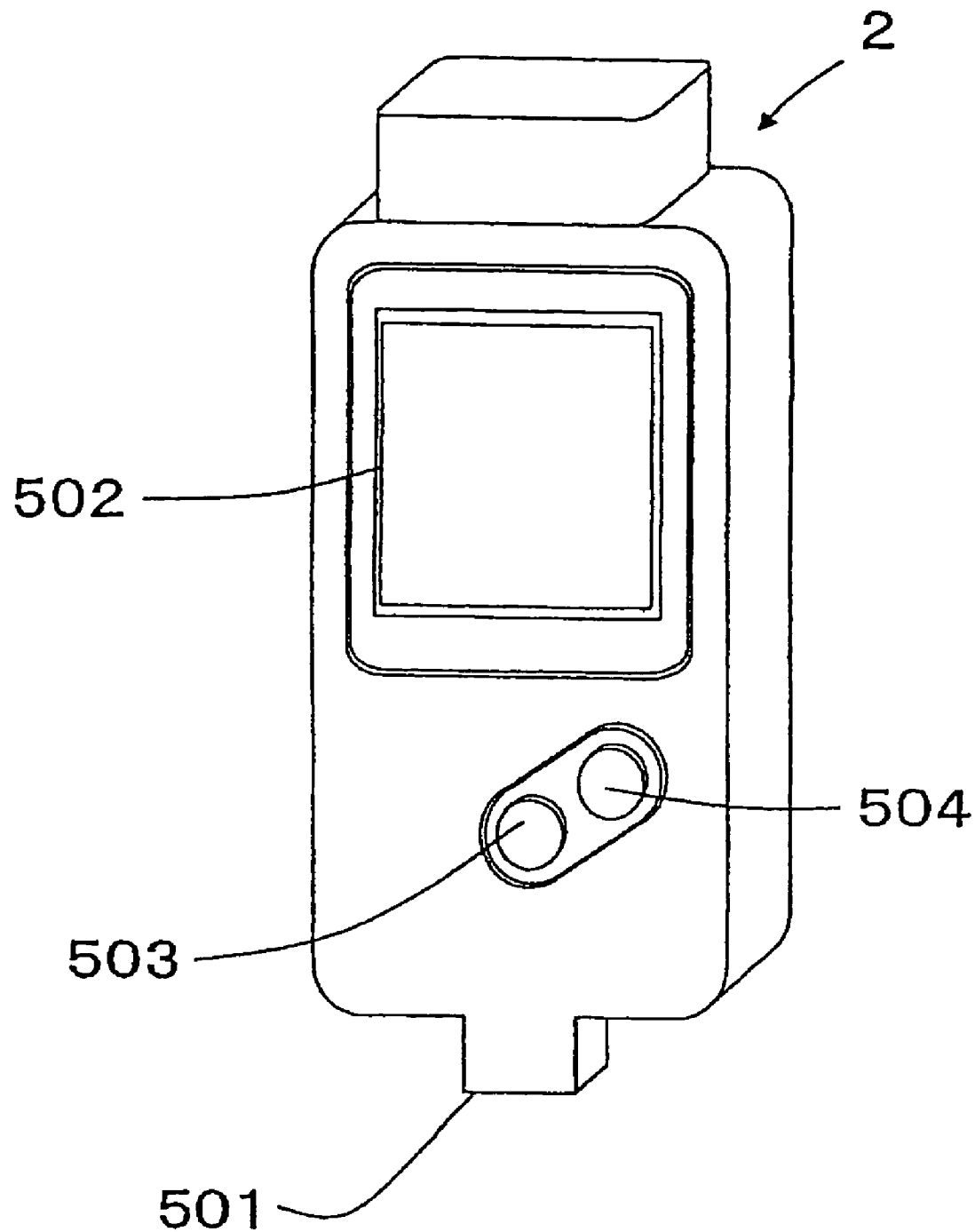

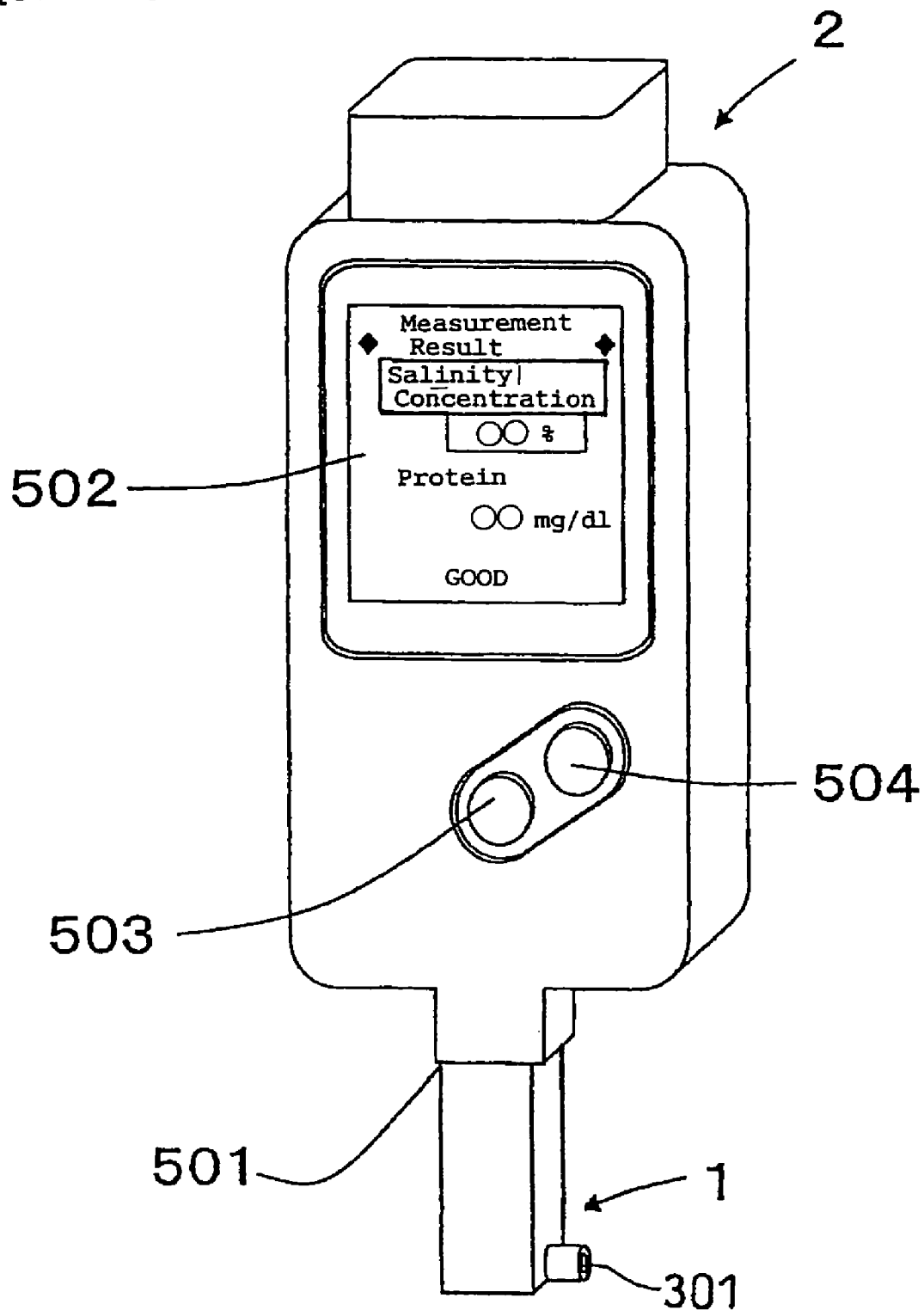
[FIG.14]

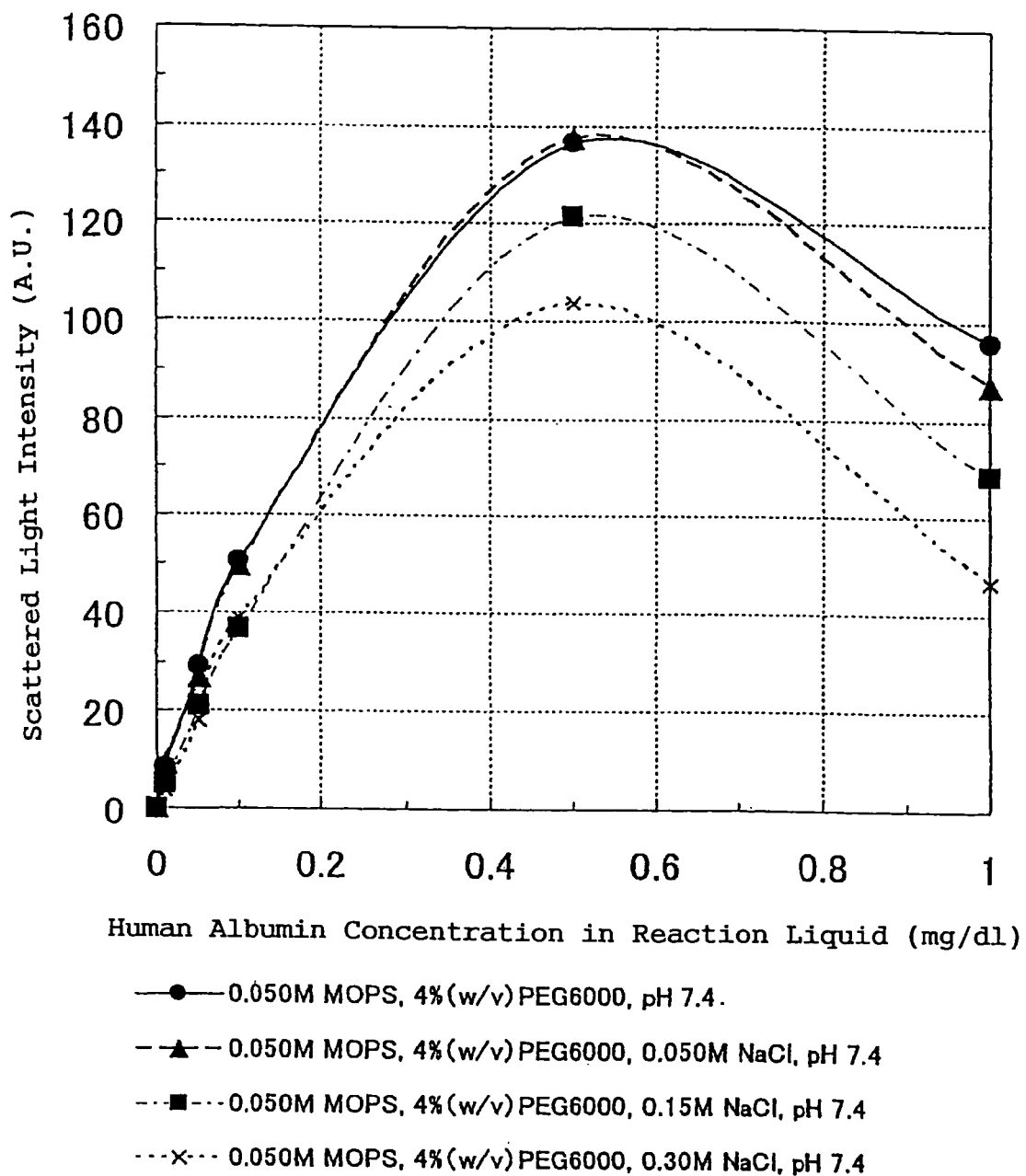
[FIG.15]

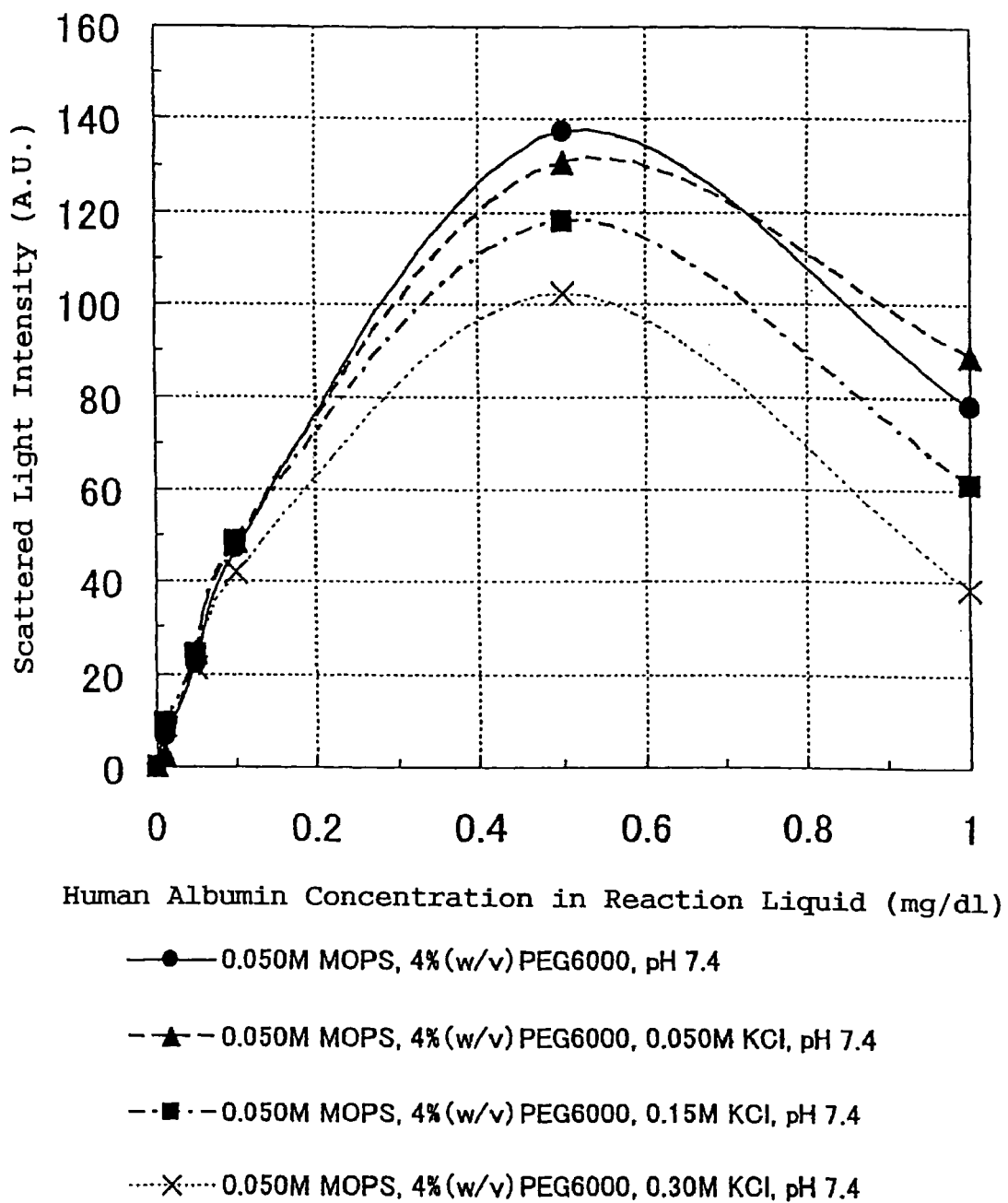

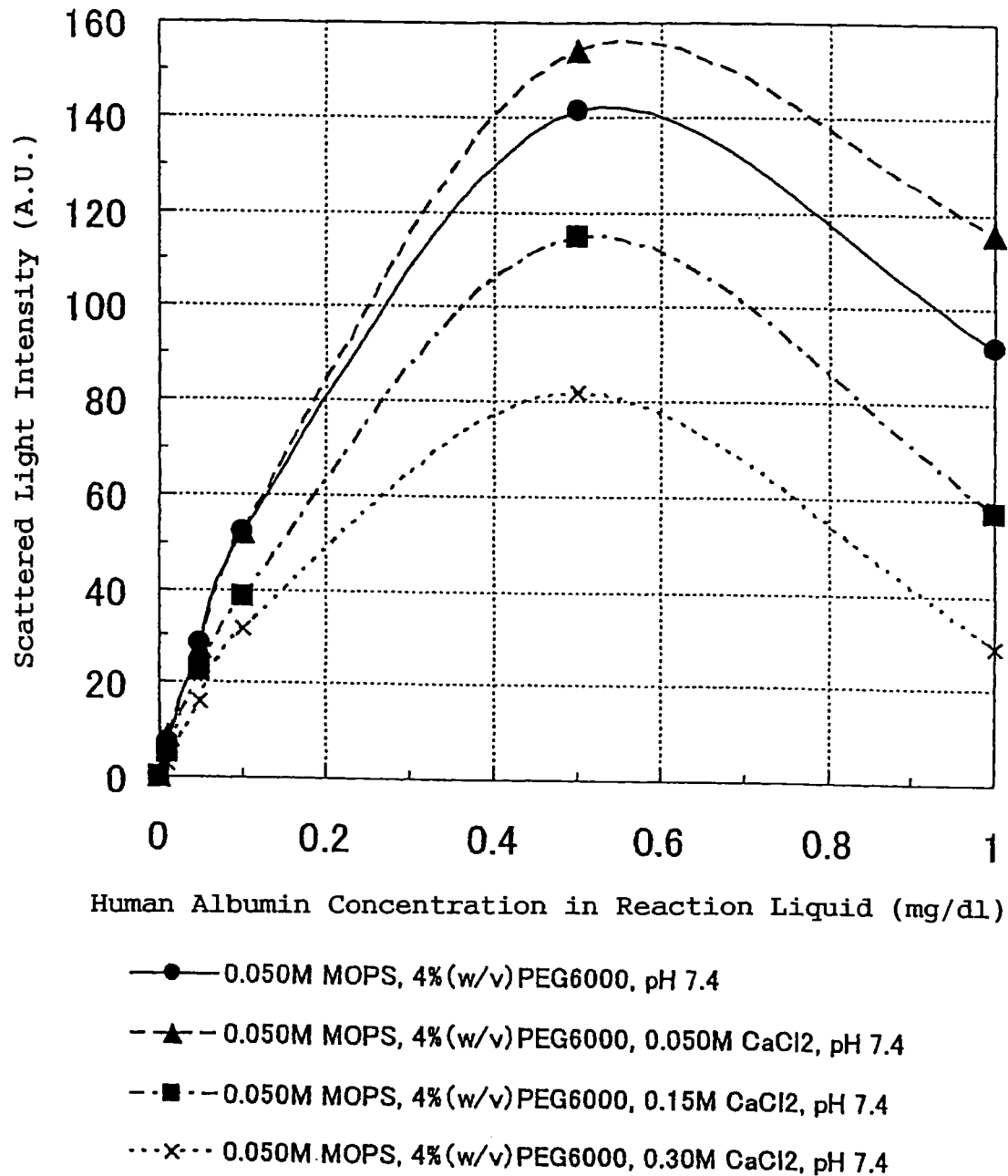
[FIG.17]

SENSOR, MEASURING DEVICE, AND MEASURING METHOD

RELATED APPLICATIONS

This application is a national phase of PCT/JP2005/007727 filed Apr. 22, 2005, which claims priority from Japanese Application No. 2004-137075 filed May 6, 2004, the disclosures of which Applications are incorporated by reference herein. The benefit of the filing and priority dates of the International and Japanese Applications is respectfully requested.

TECHNICAL FIELD

The present invention relates to sensors for measuring a plurality of items of a sample, and to a measuring device and a measuring method using the sensor.

BACKGROUND ART

Measuring devices that are conventionally used in the field of clinical testing are mainly large-scale automated devices and POCT (Point of Care Testing) devices.

The large-scale automated devices are provided at a central clinical-testing department of hospitals and at companies that mainly undertake clinical testings, and by using these devices, a sample of many patients can be tested for a plurality of items (for example, Patent Publication Document 1). For example, a large automated device manufactured by Hitachi, Ltd., type 7170, is capable of completing 800 tests/hour on 36 items at maximum. Therefore, the large-scale automated device has been contributing to efficiency in testing, which makes it suitable for hospitals with a large number of examinee.

On the other hand, POCT devices are used for clinical testing conducted in medical field other than a testing room and a testing center of hospitals, and include devices used in at-home medical care (for example, Patent Publication Document 2 and Patent Publication Document 3). For example, a blood-sugar sensor, a pregnancy test reagent, an ovulation test reagent, and an HbA1c and microalbumin testing device (for example, DCA2000 manufactured by Bayer AG) may be mentioned. These POCT devices are less applicable for all-purpose use compared with large-scale automated devices, but capable of easy and quick measurement by focusing on a marker substance unique to a disease. Thus, the devices are effective for screening and monitoring examinees. Additionally, the POCT devices are small and portable, can be introduced for low costs, and further usable for anyone without particular specialties in terms of operation.

There are many measuring items currently for clinical test. When a body fluid such as urine is used as a sample, the measurement methods are roughly divided to an optical measurement method and an electrochemical measurement method, mainly. In the large-scale automated devices and the POCT devices, measurement is conducted by using the optical measurement method or electrochemical measurement method.

Recently, a rise in medical expense and an increase in lifestyle-related disease patient have been causing a strain on medical economy, and a reduction in medical expense and avoidance on increase in lifestyle-related disease patient have been problems. As a fundamental solution for such problems, Evidence Based-Medical (EBM) has been considered. By conducting EBM, medical care can be managed objectively for a respective patient. Then, by practicing preventive medical care based on EBM, a control on the number of the lifestyle-related disease patient particularly is particularly expected.

For establishing and practicing the EBM, test information from clinical tests is essential information. Test information in EBM includes test results and solutions for patient based on the results. The solutions for patients refer to instructions on daily habit such as meal management and treatment by medication. That is, the testing in the EBM can be evaluated as "task-setting" and "policy-determining" for those who are to receive medical care. Therefore, in EBM, to provide safe and substantial solution with further feeling of security, it is necessary to clearly present the problem for those who are to receive medical care. Thus, in clinical testing, it is important to know each of the test result easily and quickly on a plurality of interrelated test items.

Conventional large-scale automated device as in the above are applicable for all-purpose, and many items can be tested regardless of presence or absence of relevance to the disease. However, the complicated structure of the device makes the operation difficult for those without expertise, and further, there are problems in that it takes long to obtain test results, and involves a longer time for giving the feedback of the results to the examinee. Additionally, although the above POCT device is excellently operable and is capable of easy and quick test, it is a measuring device specially for a marker related to a specific disease, and is not capable of testing a plurality of items.

Thus, there has been proposed a device comprising a cavity to which a sample liquid flows in by capillary effects; being used for biochemical or clinical examination; and having an electrode structure for measuring the sample's electrochemical characteristics, and a reagent such as antibody and enzyme capable of being released in the cavity; wherein a wall of the cavity is transparent so that the inner cavity can be optically measured (for example, Patent Publication Document 4).

[Patent Publication Document 1] JP 09-127126 A
[Patent Publication Document 2] JP 07-248310 A
[Patent Publication Document 3] JP 03-046566 A
[Patent Publication Document 4] U.S. Pat. No. 5,141,868B

DISCLOSURE OF THE INVENTION

Problem to be Solved by the Invention

However, there was a problem in the structure of the device described in Patent Publication Document 4 in that the reagent used for the optical measurement dissolves in the sample supplied in the cavity and reaches the electrode structure, giving adverse effects to the measurement of electrical characteristics with the electrode structure.

Thus, in view of such conventional problems, the present invention aims to provide a sensor having simple structure, and being capable of measuring a plurality of items accurately and quickly by simultaneously carrying out an optical measurement and an electrochemical measurement of a sample. Also, the present invention aims to provide a measuring device and a measuring method capable of measuring a plurality of items quickly and accurately by using the sensor.

Means for Solving the Problem

That is, to solve the above problems, the present invention provides a sensor comprising:
a sample-holding unit for holding a sample including an analyte;
a sample-supplying port for supplying the sample to the sample-holding unit;
a detecting unit for carrying out an electrochemical measurement, the unit being provided in the sample-holding unit;
an optical measuring unit for carrying out an optical measurement, the unit being provided in the sample-holding unit; and
a reagent-holding unit for holding a reagent for the optical measurement, the unit provided in the sample-holding unit;
wherein in a flowing direction of the sample supplied from the sample-supplying port in the sample-holding unit, the sample-supplying port, the detecting unit, and the reagent-holding unit are positioned in the order recited.

Also, the present invention provides a measuring device comprising:
a sensor-attaching unit for attaching the sensor;
a light source for releasing incident light that entered the optical measuring unit of the sensor;
a light-receiving unit for receiving the exit light outputted from the optical measuring unit;
a voltage-applying unit for applying a voltage to the detecting unit;
an electric-signal measuring unit for measuring an electric-signal from the detecting unit; and
a processing unit for detecting or quantifying the analyte based on at least one of the exit light received from the light-receiving unit and the electric-signal measured by the electric-signal measuring unit.

Further, the present invention provides a measuring method for an analyte using a sensor comprising:
a sample-holding unit for holding a sample including a first analyte and a second analyte;
a sample-supplying port for supplying the sample to the sample-holding unit;
a detecting unit for carrying out an electrochemical measurement, the unit being provided in the sample-holding unit;
a light-entrance unit for introducing incident light to the sample-holding unit, the unit being provided in the sample-holding unit;
a light-exit unit for releasing exit light from inside the optical measuring unit to outside the optical measuring unit, the unit being provided in the sample-holding unit; and
a reagent-holding unit for holding a reagent for the optical measurement, the unit being provided in the sample-holding unit;
wherein in a flowing direction of the sample supplied from the sample-supplying port in the sample-holding unit, the sample-supplying port, the detecting unit, and the reagent-holding unit are positioned in the order recited;
the method comprising the steps of:
(A) supplying the sample to the sample-holding unit;
(B) applying a voltage to the detecting unit;
(C) measuring an electric-signal from the detecting unit;
(D) detecting or quantifying the second analyte based on the electric-signal measured in the step (C);
(E) applying incident light to the sample held in the sample-holding unit via the light-entrance unit;
(F) measuring exit light released from inside the sample-holding unit to outside the sample-holding unit via the light-exit unit, caused by the application of the incident light; and
(G) detecting or quantifying the first analyte based on the exit light measured in the step (F).

Effect of the Invention

Based on the present invention, with a sensor having a simple structure as noted in the above, an optical measurement and an electrochemical measurement of a sample can be done simultaneously, and a plurality of items can be measured quickly and accurately. Especially, although there is a problem in that usually a reagent used for the optical measurement gives adverse effects on an electrochemical measurement, based on the above structure, such problem can be solved. Further, based on the present invention, with the use of the sensor, a measuring device and a measuring method in which a plurality of items can be measured quickly and accurately can be realized.

BRIEF DESCRIPTION OF THE DRAWINGS

[FIG. 1] A perspective view illustrating Embodiment 1 of a sensor of the present invention.

[FIG. 2] A perspective view of the sensor seen from the direction of arrow B in FIG. 1.

[FIG. 3] A cross section at lines A-A in FIG. 1.

[FIG. 4] A perspective view illustrating Embodiment 2 of a sensor of the present invention.

[FIG. 5] A perspective view of the sensor seen from the direction of arrow B in FIG. 4.

[FIG. 6] A cross section at lines A-A in FIG. 4.

[FIG. 7] A perspective view illustrating Embodiment 3 of a sensor of the present invention.

[FIG. 8] A perspective view of the sensor seen from the direction of arrow B in FIG. 7.

[FIG. 9] A cross section at lines A-A in FIG. 7.

[FIG. 10] A perspective view illustrating a measuring device 2 in Embodiment 4 of the present invention.

[FIG. 11] A perspective view the of the measuring device 2 shown in FIG. 10 with the sensor 1 of Embodiment 1 attached.

[FIG. 12] A block diagram illustrating a structure of the measuring device 2.

[FIG. 13] A perspective view illustrating a measuring device 2 of Embodiment 5 of the present invention.

[FIG. 14] A perspective view of the measuring device 2 shown in FIG. 13 with the sensor 1 of Embodiment 3 attached.

[FIG. 15] A graph showing the relationships between human albumin concentrations and scattered light intensity in reaction liquids with respective salt concentrations, in the case when NaCl was added to the reaction liquid, in Examples.

[FIG. 16] A graph showing the relationships between human albumin concentrations and scattered light intensity in reaction liquid with respective salt concentrations in the case when KCl was added to the reaction liquid, in Examples.

[FIG. 17] A graph showing the relationships between human albumin concentrations and scattered light intensity in reaction liquids with respective salt concentrations in the case when $CaCl_2$ was added to the reaction liquid, in Examples.

BEST MODE FOR CARRYING OUT THE INVENTION

1. Sensor

A sensor of the present invention comprises:

a sample-holding unit for holding a sample including an analyte;

a sample-supplying port for supplying a sample to the sample-holding unit;

a detecting unit for carrying out an electrochemical measurement, the unit being provided in the sample-holding unit;

an optical measuring unit for carrying out an optical measurement, the unit being provided in the sample-holding unit; and a reagent-holding unit for holding a reagent for the optical measurement, the unit being provided in the sample-holding unit;

wherein in the flowing direction of the sample supplied from the sample-supplying port in the reagent-holding unit, the sample-supplying port, the detecting unit, and the reagent-holding unit are disposed in the order mentioned.

Based on such structure, by supplying a sample once from the sample-supplying port to the sample-holding unit, the optical measurement and the electrochemical measurement for the sample can be carried out almost simultaneously with a use of one sensor, and a plurality of items can be measured easily and quickly.

Additionally, in the flowing direction of the sample supplied from the sample-supplying port in the sensor, the detecting unit is located upstream of the reagent-holding unit, retarding a dissolution of the reagent used for the optical measurement in the sample supplied to the sample-holding unit to reach the detecting unit, and keeping to the minimum the problem of adverse effects from the reagent to be used for the optical measurement on the electrochemical measurement.

The sensor of the present invention may be formed with a container comprising mainly a sample-holding unit and a sample-supplying port for supplying a sample to the sample-holding unit, and various forms may be applied to the extent that is not detrimental to the effects of the present invention.

As the materials forming the above sensor, as long as at least the optical measuring unit to be described later is formed with a light transmitting material, units such as the sample-holding unit may be formed with various materials without particular limitation, to the extent that is not detrimental to the effects of the present invention. As the above light transmitting material, for example, quartz, polystyrene, and the like may be mentioned.

In view of cost reduction and manufacturing process simplification, the whole sensor is preferably formed of a single material. Also, when a sensor is to be made disposable, polystyrene is used preferably in view of cost reduction.

The detecting unit is provided in the sample-holding unit, and preferably is provided at a position different from an optical path of incident light introduced to the sample-holding unit and an optical path of exit light released from the sample-holding unit. Based on such structure, the detecting unit does not block the incident light and the exit light, and an excellent optical measurement can be conducted on the sample supplied into the sample-holding unit.

For example, when the sample-holding unit has a rectangular parallelepiped form, each of a light-entrance unit and a light-exit unit may be provided at a face of the rectangular parallelepiped body, the face being different from each other, and the detecting unit may be provided at a face different from the faces on which the light-entrance unit and the light-exit unit are provided.

In the flowing direction of the sample supplied from the sample-supplying port in the sample-holding unit, the optical measuring unit is preferably located at about the same position with the reagent-holding unit or downstream of the reagent-holding unit. Based on such structure, the reagent used for the optical measurement is dissolved in the sample supplied into the sample-holding unit, and then the sample including the reagent reaches the optical measuring unit, thereby enabling a quick optical measurement without forced stirring in the sample-holding unit.

The reagent-holding unit is provided inside the above sample-holding unit. That is, in the sensor of the present invention, a reagent used for the optical measurement is provided in the reagent-holding unit. The reagent is preferably carried in the sample-holding unit and/or the above sample-introducing path in a dried condition. Based on this, the dried and carried reagent can be dissolved in the sample when the sample is supplied into the sample-holding unit and/or the sample-introducing path.

For example, the reagent may be carried by impregnating a porous carrier formed of a glass fiber or a filter paper with a reagent solution and drying, and the barrier may be placed in the sample-holding unit and/or the sample-introducing path. The reagent may be carried by directly applying the reagent solution on a wall forming the sample-holding unit and/or the sample-introducing path, and drying.

The reagent preferably reacts uniquely with the analyte in the sample. Based on this, since the reaction is the one specific to the analyte, presence of the specific analyte can be checked easily from the sample in which a plurality of substances (further, a plurality of the analyte) are mixed.

For the specific reaction between the reagent and the analyte in the sample, antigen-antibody reaction using an antibody reagent, biochemical reaction, and the like may be mentioned. For the biochemical reaction, for example, CBB G-255 method and Pyrogallol Red method used for urine protein measurement, and Benedict method and Nylander method used for urinary sugar measurement may be mentioned.

For the reagent used for the specific reaction with the analyte, for example, an enzyme, an antibody, a hormone receptor, a chemiluminescence reagent, and a DNA may be mentioned. Among these, usage of an antibody is advantageous in that an antibody capable of specifically bonding with various analytes can be produced by known methods, and a reagent can be made easily.

For example, by immunizing a mouse and a rabbit using a protein such as albumin or a hormone such as hCG and LH as an antigen, an antibody for the antigen can be obtained. For the antibody, an antibody to a protein such as albumin contained in urine, and an antibody to a hormone such as hCG and LH contained in urine may be mentioned.

The optical measuring unit preferably comprises a light-entrance unit for introducing incident light, and a light-exit unit for releasing outgoing light from inside of the optical measuring unit to the outside of the optical measuring unit.

Based on such structure, the optical path of the incident light and the optical path of the outgoing light can be defined, and scattered light, transmitted light, and reflected light can be measured easily and reliably.

In the sensor of the present invention, for an element forming the detecting unit, for example, a glass electrode, an electrode formed of a metal such as copper, platinum, and the like, an electrode formed of a semiconductor such as polysilicon and the like, a transistor such as a Field Effect Transistor (FET) and the like may be mentioned.

Among these, the detecting unit preferably comprises at least a pair of electrodes for measuring a conductivity of the sample. Based on such structure, a salt concentration measurement of the sample can be carried out easily and reliably in addition to the optical measurement. Also, in the case when the salt concentration influences the optical measurement results, correction of the measurement value of the optical measurement can be done easily as well.

Additionally, in the sensor of the present invention, the detecting unit preferably includes an ion-selective electrode (ISFET: Ion Selective FET), and a reference electrode that functions as a comparative electrode. For the ion-sensitive electrode, a conventional, known one may be used, for example. And the ion-sensitive electrode may comprise an electrode and an ion-sensitive film provided to cover at least a portion of the electrode.

For the ion-sensitive film, those with a function of selectively passing any of the ions among sodium ion, potassium ion, lithium ion, magnesium ion, calcium ion, chloride ion, ammonium ion, hydrogen ion, and the like may be used.

For the compound forming the ion-sensitive film, known inclusion compounds may be used according to the ion to be passed. For the sodium ion, for example, Bis[(12-crown-4)methyl]2,2-dibenzomalonate and the like may be mentioned, and for the potassium ion, for example, bis[(benzo15-crown-5)4-methyl]pimelate and the like may be mentioned. For the lithium ion, for example, phosphododecyl-14-crown-4 and the like may be mentioned, and for the magnesium ion, for example, 4,13-bis[N-(1-adamantyl)carbamoylacetyl]-8-tetradecyl-1,7,10,16-tetraoxa-4,13-diazacyclooctadecane and the like may be mentioned.

For the calcium ion, for example, 4,16-bis(N-octadecylcarbamoyl)-3-octbutyryl-1,7,10,13,19-pentaoxa-4,16-diazacyclohenicosane and the like may be mentioned, and for the chloride ion, for example, 2,7-Di-tert-butyl-9,9-dimethyl-4,5-bis(N-n-butylthioureylene)xanthene and the like may be mentioned.

Further, for the ammonium ion, for example, 2,6,13,16,23,26-hexaoxaheptacyclo-[25.4.4.4$^{7,12}$.4$^{17,22}$.0$^{1,17}$.0$^{7,12}$.0$^{17,22}$] tritetracontane and the like may be mentioned.

Any of the above inclusion compounds may be obtained for example from DOJINDO LABORATORIES as a commercially available product.

For a method for forming the ion-sensitive film on the electrode, various methods may be used. For example, the ion-sensitive film may be formed by dissolving the inclusion compound, a polymer compound such as a plasticizer, an anion remover, and polyvinyl chloride (PVC) in an organic solvent, and applying the obtained solvent mixture on the electrode and then drying by air.

2. Measuring Device

Then, a measuring device of the present invention comprises:

a sensor-attaching unit for attaching the sensor;

a light source for releasing an incident light that entered the optical measuring unit of the sensor;

a light-receiving unit for receiving exit light that exited the optical measuring unit;

a voltage-applying unit for applying a voltage to the detecting unit;

an electric-signal measuring unit for measuring an electric-signal from the detecting unit; and a processing unit for detecting or quantifying the analyte based on at least one of the exit light received by the light-receiving unit and the electric-signal measured by the electric-signal measuring unit.

Based on such structure, by supplying a sample from the sample-supplying port to the sample-holding unit of the above sensor once, an optical measurement and an electrochemical measurement of the sample can be carried out almost simultaneously with a use of one measuring device, and a plurality of items can be measured easily and quickly.

Additionally, since in the sensor used, the detecting unit is located upstream of the reagent-holding unit in the flowing direction of the sample supplied from the sample-supplying port in the sensor as mentioned above, it retards a dissolution of the reagent used for the optical measurement in the sample supplied to the sample-holding unit to reach the detecting unit, and therefore adverse effects from the reagent used for the optical measurement on the electrochemical measurement can be kept to the minimum.

Here, the sensor is preferably removably attached to the measuring device. Also, the sensor is preferably disposable.

The measuring device of the present invention preferably further comprises a suction unit for sucking the sample, in the sample-holding unit of the sensor attached to the sensor-attaching unit. Based on such structure, the sample can be supplied into the sample-holding unit of the sensor by using the suction unit, with the sensor attached to the sensor-attaching unit. The suction unit may be operated manually or automatically. For example, a piston mechanism similar to a syringe, a dispenser, and the like may be mentioned.

Although the piston operation method may be manual or automatic, the automatic operation is preferable for decreasing a burden on the operator. The automation method includes operating a piston with a motor. For the motor, a step motor, a direct-current motor, and the like may be mentioned. The step motor is a motor that rotates in a specific rotation angle per one pulse signal entered, and since the rotation angle can be determined by the pulse number, an encoder for positioning is unnecessary. That is, the operation distance of the piston can be controlled by the entered pulse number. By converting the motor's rotating motion to linear motion with use of a linear mechanism of a combination of a gear mechanism, a male screw, and a female screw, the piston is operated. Although the manner of converting the rotating motion to linear motion is the same in the case of the direct-current motor as well, in the case of the direct-current motor, to control the piston's operation distance, an encoder for detecting motor's rotating position becomes necessary. There is also a linear-type step motor, and in this type of motor, a linear mechanism of a combination of a male screw and a female screw is incorporated in the motor, and it is structured so that a bar-like movable unit carries out linear motion depending upon the entered pulse number. Thus, the piston can be connected directly to this bar, achieving a simple structure.

The measuring device of the present invention preferably comprises a recording unit for recording in a storage medium the results of detecting or quantifying the analyte in the sample at the processing unit.

Based on such structure, results of the detection or quantification can be stored in the removable storage medium, and the results can be easily taken out from the measuring device. Thus, the storage medium can be brought or sent to an analysis specialist and an analysis can be requested easily.

Additionally, the measuring device of the present invention preferably comprises:

a clock unit for timing the time taken for detecting or quantifying the analyte in the sample at the processing unit; and a memory unit for memorizing the results of the detection or quantification of the analyte in the sample at the processing unit, in association with the detection or quantification time timed at the clock unit.

Based on such structure, since the results of the detection or quantification of the analyte in the sample are stored in the memory unit along with the measured time, an economic analysis can be done.

Further, the measuring device of the present invention preferably comprises a sending unit for sending the results of detecting or quantifying the analyte in the sample at the processing unit, to outside the measuring device. Based on such structure, the results of the detection or quantification on the analyte in the sample can be sent to an analysis-related department in a hospital, analysis-related business provider, and the like, and can be analyzed at the analysis-related department, analysis-related business provider, and the like. Thus, the time taken from the measurement to the analysis can be shortened.

Also, the measuring device of the present invention preferably comprises a receiving unit for receiving the results of the analysis at the analysis-related department or the analysis-related business provider. Based on such structure, feedback on the results of the analysis can be given to examinees quickly.

3. Measuring Method

The measuring method of the present invention is a measuring method including the above-mentioned sensor of the present invention, and the sample including a first analyte and a second analyte, the method including the steps of:

(A) supplying the sample to the sample-holding unit;

(B) applying a voltage to the detecting unit;

(C) measuring an electric-signal from the detecting unit;

(D) detecting or quantifying the second analyte based on the electric-signal measured in the step (C);

(E) applying incident light to the sample held in the sample-holding unit via the light-entrance unit;

(F) measuring exit light that exited the sample-holding unit to outside the sample-holding unit via the light-exit unit, caused by the application of incident light; and (G) detecting or quantifying the first analyte based on the exit light measured in the step (F).

Based on such structure, by supplying a sample from the sample-supplying port to the sample-holding unit once, an optical measurement and an electrochemical measurement of the sample can be carried out almost simultaneously with a use of one measuring device, and a plurality of items can be measured easily and quickly.

Additionally, since the detecting unit is located upstream of the reagent-holding unit in the flowing direction of the sample supplied from the sample-supplying port in the sensor, it retards a dissolution of the reagent used for the optical measurement in the sample supplied to the sample-holding unit to reach the detecting unit, and therefore adverse effects from the reagent used for the optical measurement on the electrochemical measurement can be kept to the minimum.

Here, the measuring method of the present invention preferably includes the steps of:

sucking a sample liquid by a suction unit from the sample-supplying port of the sensor attached to the sensor-attaching unit;

detecting the supply of the sample to the sample-holding unit based on a change of an electric-signal from the detecting unit; and activating a light source based on the detection of the sample in the step.

Particularly, the incident light is preferably applied in the step (E), when the electric-signal is detected in the step (C). Based on such structure, a supply of a sample into the sample-holding unit can be detected automatically and a preparation of the optical measurement can be done at the same time, thereby shortening the time required for carrying out the electrochemical measurement and the optical measurement.

Further, based on any one of the quantification results of the first analyte and the quantification results of the second analyte, a step is preferably included for correcting the other of the quantification results. Based on such structure, by measuring a plurality of items that are interrelated, accuracy in measurement results can be improved.

Here, for samples in the present invention, a body fluid such as urine, serum, plasma, and blood and a supernatant liquid of a culture medium may be mentioned.

When the sensor and measuring device of the present invention are to be used for the purpose of in-home daily health management, the measurements are preferably noninvasive, and thus urine is preferable as a sample.

For the first analyte, for example, albumin, hCG, LH, CRP, and IgG may be mentioned.

For the second analyte, for example, at least one of sodium ion, potassium ion, lithium ion, magnesium ion, calcium ion, chloride ion, ammonium ion, and hydrogen ion may be mentioned.

In a urine qualitative test conducted in an initial stage of health management, twelve items are tested, namely, pH, specific gravity, protein, sugar, occult blood, ketone body, bilirubin, urobilinogen, nitrite, leukocyte, ascorbic acid, amylase, and sodium chloride. For the purpose of analyzing kidney function, microalbumin is tested, and for a marker for a pregnancy test and an ovulation test, hormones such as hCG and LH are used.

Roughly dividing the above test items, optical measurement based on antigen-antibody reactions is suitable for tests for protein, microalbumin, and hormones such as hCG and LH. Here, for the optical measurement based on antigen-antibody reactions, for example, nephelometric immunoassay, turbidimetric immunoassay, and latex agglutination immunoassay may be used.

On the other hand, salinity (sodium ion, potassium ion, and the like) and pH of urine are mainly measured based on electrochemical measurement. Particularly, salinity of urine reflects daily habit such as meal, and is the important information for providing a solution related to health management.

The salinity and pH in urine differs by sample due to circadian variation, non-circadian variation, and individual differences, and this difference in sample give influence on reaction amount of the antigen-antibody reaction obtained by the optical measurement. Especially, a change in salinity concentration greatly influences the reaction results in nephelometric immunoassay, turbidimetric immunoassay, and latex agglutination immunoassay. For example, an antigen-antibody reaction in a high salinity concentration is higher in dissociation degree and less in reaction amount.

Therefore, the antigen concentration obtained in the optical measurement is preferably corrected by using data showing relationships between the antigen concentration and exit light intensity in a plurality of salinity concentrations as calibration curve, and by using salinity values obtained in a conductivity measurement (electrochemical measurement).

Based on this, sample differences can be corrected. In this way, accuracy of quantitative results can be improved.

Further, by using the already mentioned ion-sensitive film in the ion-sensitive electrode, and obtaining concentrations of sodium ion and potassium ion, i.e., main components of salinity in urine, a correction in view of difference of each ion's influence on the antigen-antibody reaction is also possible.

Also, by obtaining pH of urine from the measurement of the hydrogen ion concentration, a correction in a consideration of effects from pH is possible as well.

In the following, embodiments of a structure of the sensor of the present invention are described further in detail with reference to the drawings. However, the present invention is not limited to these embodiments.

Embodiment 1

A structure of a sensor in this embodiment is described by using FIGS. 1 to 3. The sensor in this embodiment is structured with an intension of using a scattered light for the optical measurement. FIG. 1 is a perspective view showing Embodiment 1 of the sensor of the present invention. FIG. 2 is a perspective view of the sensor seen from the direction of arrow B in FIG. 1. FIG. 3 is a cross section at lines A-A in FIG. 1.

As shown in FIG. 1, a sensor 1 in this embodiment is formed with a sample-holding unit 104 formed of polystyrene.

The sample-holding unit 104 has a form of a combination of a hollow quadrangular pyramid and a hollow quadrangular prism with square cross sections, and at a tip of the quadrangular pyramid, a sample-supplying port 101 is provided. Also, on the opposite side of the sample-supplying port 101, an opening 102 is provided. Then, the sensor in this embodiment is structured so that a sample is supplied from the sample-supplying port 101 to the sample-holding unit 104.

On a first face among the four faces surrounding the sample-holding unit 104, as shown in FIG. 3, a reagent-holding unit 108 is formed by sticking a glass-fiber-made porous carrier in which an antibody to human albumin in urine is carried under dry conditions as a reagent.

Also, among the faces different from the first face where the reagent-holding unit 108 is formed, on a second face adjacent to the above first face, a detecting unit 111 comprising an ion-sensitive electrode 105 and a reference electrode 106 is provided between the sample-supplying port 101 and the reagent-holding unit 108.

That is, in a flowing direction of a sample supplied from the sample-supplying port 101 in the sensor 1 (direction of arrow X that is substantially parallel to the longitudinal direction of the sensor 1), the sample-supplying port 101, the detecting unit 111, and the reagent-holding unit 108 are positioned in the order mentioned, and distance $D_1$ from the sample-supplying port 101 to the detecting unit 111 and distance $D_2$ from the sample-supplying port 101 to the reagent-holding unit 108 satisfy the relation formula: $D_1 < D_2$.

The detecting unit 111 has a silicon substrate. By forming a gate, a source, and a drain on the silicon substrate and providing an ion-sensitive film for covering the gate, an ion-sensitive electrode 105 is formed. The ion-sensitive film is formed of Bis[(12-crown-4)methyl]2,2-dibenzomalonate which specifically recognizes sodium ion.

Also, a reference electrode 106 is disposed on the above silicon substrate, an insulating film 113 is provided so as to expose the reference electrode 106 and the ion-sensitive film, while covering other portions.

Also, among the faces of the above silicon substrate, on the opposite face of the face where the ion-sensitive electrode 105 and the reference electrode 106 are provided, a terminal is provided (not shown) for each of the gate, the source, and the drain of the ion-sensitive electrode 105, and for the reference electrode 106. These terminals are connected to three terminals 107 provided at the opening 102 of the sample-holding unit 104, via lead wires 112 protected with an insulating film. As shown in FIG. 2, the three terminals 107 are extended to the rear face of the inner-wall face, from the inner-wall face of the sample-holding unit 104 via the opening 102. The gate and the source are connected to the same terminal, and each of the drain and the reference electrode 106 is connected to a different terminal.

Among four faces forming the sample-holding unit 104, the two faces other than the face provided with the detecting unit 111 and the face provided with the reagent-holding unit 108 function as a light-entrance unit 109 and as a light-exit unit 110.

Embodiment 2

A structure of a sensor in this embodiment is described by using FIGS. 4 to 6. The sensor in this embodiment is structured with an intension of using a transmitted light for the optical measurement. FIG. 4 is a perspective view showing Embodiment 2 of the sensor of the present invention. FIG. 5 is a perspective view of the sensor seen from the direction of arrow B in FIG. 4. FIG. 6 is a cross section at lines A-A in FIG. 4.

As shown in FIG. 4, a sensor 1 in this embodiment is formed with a sample introducing unit 203 formed of polystyrene, and a sample-holding unit 204. The sample introducing unit 203 and the sample-holding unit 204 are formed integrally.

The sample introducing unit 203 has a cylindrical form, with a sample-supplying port 201 provided on a tip thereof. Also, the sample-holding unit 204 has a form of a hollow quadrangular prism with square cross sections, and on the opposite side of the sample-supplying port 201, an opening 202 is provided. Then, the sensor in this embodiment is structured so that the sample is supplied to the sample-holding unit 204 from the sample-supplying port 201 via a sample-introducing path 203.

On a first face among the four faces surrounding the sample-holding unit 104, as shown in FIG. 6, a reagent-holding unit 208 is formed by sticking a glass-fiber-made porous carrier in which an antibody to human albumin in urine is carried under dry conditions as a reagent.

Among the faces different from the first face where the reagent-holding unit 208 is formed, on the second face opposing the first face mentioned above, a detecting unit 211 comprising an ion-sensitive electrode 205 and a reference electrode 206 is provided between the sample-supplying port 201 and the reagent-holding unit 208.

That is, in a flowing direction of a sample supplied from the sample-supplying port 201 in the sensor 1 (direction of arrow X that is substantially parallel to the longitudinal direction of the sensor 1), the sample-supplying port 201, the detecting unit 211, and the reagent-holding unit 208 are positioned in the order mentioned. And distance $D_1$ from the sample-supplying port 201 to the detecting unit 211, and distance $D_2$ from the sample-supplying port 201 to the reagent-holding unit 208 satisfy the relation formula: $D_1 < D_2$.

The detecting unit 211 has a silicon substrate. By forming a gate, a source, and a drain on the silicon substrate and providing an ion-sensitive film for covering the gate, an ion-sensitive electrode 205 is formed. The ion-sensitive film is formed of Bis[(12-crown-4)methyl]2,2-dibenzomalonate which specifically recognizes sodium ion.

Additionally, a reference electrode 206 is disposed on the above silicon substrate, and an insulating film 213 is provided so as to expose the reference electrode 206 and the ion-sensitive film, while covering other portions.

Also, among the faces of the above silicon substrate, on the opposite face of the face where the ion-sensitive electrode 205 and the reference electrode 206 are provided, a terminal is provided (not shown) for each of the gate, the source, and the drain of the ion-sensitive electrode 205, and for the reference electrode 206. These terminals are connected to three terminals 207 provided at the opening 202 of the sample-holding unit 204, via lead wires 212 protected with an insulating film. As shown in FIG. 5, the three terminals 207 are extended to the rear face of the inner-wall face, from the inner-wall face of the sample-holding unit 204 via the opening 202. The gate and the source are connected to the same terminal, and each of the drain and the reference electrode 206 is connected to a different terminal.

Among the four faces forming the sample-holding unit 204, the two faces other than the face provided with the detecting unit 211 and the face provided with the reagent-holding unit 208 function as a light-entrance unit 109 and as a light-exit unit 110.

Embodiment 3

A structure of a sensor in this embodiment is described by using FIGS. 7 to 9. The sensor in this embodiment is structured with an intension of using a scattered light for the optical measurement. FIG. 7 is a perspective view showing Embodiment 3 of the sensor of the present invention. FIG. 8 is a perspective view of the sensor seen from the direction of arrow B in FIG. 7. FIG. 9 is a cross section at lines A-A in FIG. 7.

As shown in FIG. 7, a sensor 1 in this embodiment is formed with a sample introducing unit 303 formed of polystyrene and a sample-holding unit 304. And the sample introducing unit 303 and the sample-holding unit 304 are integrally formed.

The sample introducing unit 303 has a cylindrical form, with a sample-supplying port 301 provided on a tip thereof. Also, the sample-holding unit 304 has a form of a bottomed hollow quadrangular prism with square cross sections, and at a lower portion of a first face among the four faces, a sample-introducing path 303 is provided. Additionally, in the sample-holding unit 304, on the opposite side of the sample-supplying port 301, an opening 302 is provided. Then, the sensor in this embodiment is structured so that the sample is supplied to the sample-holding unit 304 from the sample-supplying port 301 via the sample-introducing path 303.

On the first face mentioned above, as shown in FIG. 9, a reagent-holding unit 307 is formed by sticking a glass-fiber-made porous carrier in which an antibody to human albumin in urine is carried under dry conditions as a reagent.

Also, among the faces different from the first face where the reagent-holding unit 307 is formed, on a second face adjacent to the first face mentioned above, a detecting unit 311 comprising a pair of electrodes 305 for conducting a conductivity measurement is provided between the sample-supplying port 301 and the reagent-holding unit 307.

That is, in a flowing direction of a sample supplied from the sample-supplying port 301 in the sensor 1 (direction of arrow X that is substantially parallel to the longitudinal direction of the sensor 1), the sample-supplying port 301, the detecting unit 311, and the reagent-holding unit 307 are positioned in the order mentioned. And distance $D_1$ from the sample-supplying port 301 to the detecting unit 311, and distance $D_2$ from the sample-supplying port 301 to the reagent-holding unit 307 satisfy the relation formula: $D_1<D_2$.

The pair of electrodes 305 forming the detecting unit 311 can be formed by conventionally known methods. The electrodes 305 are connected to two terminals 307 provided at the opening 302 of the sample-holding unit 304, via lead wires 310 protected by an insulating film. As shown in FIG. 8, two terminals 306 extend to the rear faces of the inner-wall from the inner-wall of the sample-holding unit 304 via the opening 302.

Among the four faces forming the sample-holding unit 304, the two faces other than the face provided with the detecting unit 311 and the face provided with the reagent-holding unit 307 function as a light-entrance unit 308 and as a light-exit unit 309.

Embodiment 4

A structure of a measuring device in this embodiment is described by using FIGS. 10 to 12. FIG. 10 is a perspective view showing a measuring device 2 in this embodiment. FIG. 11 is a perspective view showing the measuring device 2 shown in FIG. 10 with the sensor 1 in the above Embodiment 1 attached. FIG. 12 is a block diagram illustrating a structure of the measuring device 2.

The measuring device 2 in this embodiment comprises a sensor-attaching unit 401, a display unit 402 for displaying measurement results, a sample-sucking start button 403, and a sensor removal button 404. To the sensor-attaching unit 401, the sensor 1 can be attached to the measuring device 2 by inserting the opening 102 opposite to the sample-supplying port 101 of the sensor 1.

Then, with reference to FIG. 12, a method for measuring an analyte in urine by using the sensor 1 having the structure shown in the above Embodiment 1 and the measuring device 2 in this embodiment is described.

First, by inserting a portion of the sensor 1 into the sensor-attaching unit 401 of the measuring device 2, three terminals provided in the measuring device 2 and three terminals 107 provided in the sensor 1 are brought in contact, respectively. At this time, a sensor-insertion detection switch (not shown) comprising a microswitch provided in the measuring device 2 is activated, and a CPU 601 functioning as a control-unit detects the insertion of the sensor 1, to apply a voltage to a detecting unit 603 of the sensor 1 from a voltage-applying unit 602.

In the measuring device 2, a light-receiving unit 608 is provided (not shown) so that a transmitted light and a scattered light can be measured. To be more specific, a light source 607 and a light-receiving unit 608 are provided with the sensor 1 interposed therebetween in the linear direction of the light exited from the light-exit unit 110 of the sensor 1, so that a transmitted light can be measured.

Additionally, another light-receiving unit 608 is provided on an axis that intersects with the linear direction of light exited from the light-exit unit 110 of the sensor 1 at right angles, with the sensor 1 as the center, so that a scattered light can be measured.

Then, a sample-sucking start button 403 is pressed while a portion of the sensor 1 is immersed in urine urinated in a container such as a toilet or a paper cup. By this, a piston mechanism 604, a suction unit provided in the measuring device 2, is activated, and a predetermined amount of urine is sucked into the sample-holding unit 104 from the sample-supplying port 101 of the sensor 1.

When the urine supplied into the sample-holding unit 104 reaches the detecting unit 603, potential conditions in the detecting unit 603 changes, and the electric-signal measuring unit 605 detects the changes in the electric-signal derived therefrom, thereby allowing a CPU 601 to start timing by a clock unit 606, and to shut the voltage application by a voltage-applying unit 602. The urine supplied into the sample-holding unit 104 dissolves the antibody in dry condition carried at the reagent-holding unit, thereby advancing an immune reaction with the antigen in the urine.

Then, when it is determined by the CPU 601 that a predetermined time has passed based on a signal from the clock unit 606, the CPU 601 activates a light source 607 and a voltage-applying unit 602. Light that was exited the light source 607 and entered into the sample-holding unit via the light-entrance unit 109, scattered in urine, and exited the light-exit unit 110 (scattered light) is received by a light-receiving unit 608 provided in the measuring device 2 for receiving the scattered light.

On the other hand, the electric-signal from the detecting unit 603 is measured by an electric-signal measuring unit 605. Based on this electric-signal, the CPU 601 that functions as the processing unit converts the electric-signal into the sodium concentration in urine by referring to a calibration curve showing relations of the electric-signals and the sodium concentrations stored in a memory 609, a memory unit.

In the memory 609 in the measuring device 2, a calibration curve showing relations of exit light intensities and the antigen concentrations under a plurality of sodium concentration is stored. The CPU 601 that functions as the processing unit calculates the antigen concentration based on the exit light intensity and the electric-signal, by extracting the calibration curve data on the previously measured sodium concentration, and referring to the calibration curve.

Thus obtained sodium concentration and antigen concentration are, as shown in FIG. 11, displayed on a display unit 402. Also, the thus obtained sodium concentration and antigen concentration are stored in the memory 609 along with times of day timed with the clock unit 606.

Lastly, by pressing a sensor removal button 404, a sensor removal mechanism 610 is activated, to remove the sensor 1 automatically from the measuring device 2, after the urine in the sample-holding unit 104 is discharged from the sample-supplying port 101.

Further, the obtained sodium concentration and antigen concentration can be recorded in a storage medium such as an SD card with a recording unit 611. By storing in a removable storage medium, the measurement results can be easily pulled from the measuring device 2, and therefore the storage medium can be brought to or post to analysis specialists for analysis request.

Further, the obtained sodium concentration and antigen concentration can be sent externally from a sending unit 612 to outside the measuring device 2. Based on this, the measurement result can be sent to an analysis-related department in a hospital or an analysis-related business provider, and can be analyzed at the analysis-related department or analysis-related business provider, thus shortening time from the measurement to the analysis.

Still further, a receiving unit 613 is provided for receiving the results analyzed at the analysis-related department or the analysis-related business provider. Based on this, examinees can receive the feedback on the results of the analysis immediately.

Embodiment 5

A structure of a measuring device in this embodiment is described by using FIGS. 13, 14, and 12. FIG. 13 is a perspective view showing a measuring device 2 in this embodiment. FIG. 14 is a perspective view showing the measuring device 2 shown in FIG. 13 with the sensor 1 in the above Embodiment 3 attached. FIG. 12 is a block diagram illustrating a structure of the measuring device 2.

The measuring device 2 in this embodiment comprises a sensor-attaching unit 501, a display unit 502 for displaying the measurement results, a sample-sucking start button 503, and a sensor removal button 504. To the sensor-attaching unit 501, by inserting an opening 302 opposite to a sample-supplying port 301 of the sensor 1, the sensor 1 can be attached to the measuring device 2.

Then, with reference to FIG. 12, a method for measuring an analyte in urine by using the sensor 1 having the structure shown in the above Embodiment 3 and the measuring device 2 in this embodiment is described.

First, by inserting a portion of the sensor 1 into the sensor-attaching unit 501 of the measuring device 2, two terminals provided in the measuring device 2 and two terminals 306 provided in the sensor 1 are brought in contact, respectively. At this time, a sensor-insertion detection switch (not shown) comprising a microswitch provided in the measuring device 2 is activated, and a CPU 601 functioning as a control-unit detects the insertion of the sensor 1, to apply a voltage to a detecting unit 603 of the sensor 1 from a voltage-applying unit 602.

In the measuring device 2, a light-receiving unit 608 is provided (not shown) so that a transmitted light and a scattered light can be measured. To be more specific, a light source 607 and the light-receiving unit 608 are provided with the sensor 1 interposed therebetween in the linear direction of the light exited the light-exit unit 309 of the sensor 1, so that a transmitted light can be measured.

Additionally, another light-receiving unit 608 is provided on an axis that intersects with the linear direction of light exited the light-exit unit 309 of the sensor 1 at right angles, with the sensor 1 as the center, so that a scattered light can be measured.

Then, a sample-sucking button 503 is pressed while a portion of the sensor 1 is immersed in urine urinated in a container such as a toilet or a paper cup. By this, a piston mechanism 604, a suction unit provided in the measuring device 2, is activated, and a predetermined amount of urine is sucked into the sample-holding unit 304 from the sample-supplying port 301 of the sensor 1.

When the urine supplied into the sample-holding unit 304 reaches the detecting unit 603, a resistance value between a pair of electrodes 305 (i.e., conductivity) in the detecting unit 603 changes depending upon the salinity concentration in the sample, and the electric-signal measuring unit 605 detects the changes in the electric-signal derived therefrom, thereby allowing a CPU 601 to start timing with a clock unit 606. The urine supplied into the sample-holding unit 304 dissolves the antibody in dry condition carried at the reagent-holding unit, thereby advancing an immune reaction with the antigen in the urine.

Then, when it is determined by the CPU 601 that a predetermined time has passed based on a signal from the clock unit 606, the CPU 601 activates the light source 607 and the voltage-applying unit 602. Light that exited the light source 607 and entered into the sample-holding unit via the light-entrance unit 308, scattered in urine, and exited the light-exit unit 309 (scattered light) is received by the light-receiving unit 608 provided in the measuring device 2 for receiving the scattered light.

On the other hand, the electric-signal from the detecting unit 603 is measured by the electric-signal measuring unit 605. Based on this electric-signal, the CPU 601 that functions as the processing unit converts the electric-signal into the salinity concentration in urine by referring to a calibration curve showing relations of the electric-signals and the salinity concentrations stored in a memory 609, a memory unit.

In the memory 609 in the measuring device 2, a calibration curve showing relations of exit light intensities and the antigen concentrations is stored. The CPU 601 that functions as the processing unit calculates the antigen concentration based on the exit light intensity and the electric-signal, by referring to the calibration curve.

Thus obtained salinity concentration and antigen concentration are, as shown in FIG. 14, displayed on a display unit 502. Also, the thus obtained salinity concentration and antigen concentration are stored in the memory 609 along with times of day timed with the clock unit 606.

Lastly, by pressing a sensor removal button 504, a sensor removal mechanism 610 is activated, to remove the sensor 1 automatically from the measuring device 2, after the urine in the sample-holding unit 304 is discharged from the sample-supplying port 301.

Further, the obtained salinity concentration and antigen concentration can be recorded in a storage medium such as an SD card with a recording unit 611. By storing in a removable storage medium, the measurement results can be easily pulled from the measuring device 2, and therefore the storage medium can be brought to or post to analysis specialists for analysis request.

Further, the obtained salinity concentration and antigen concentration can be sent externally from a sending unit 612 to outside the measuring device 2. Based on this, the measurement results can be sent to an analysis-related department in a hospital or an analysis-related business provider, and can be analyzed at the analysis-related department or analysis-related business provider, thus shortening time from the measurement to the analysis.

Still further, a receiving unit 613 is provided for receiving the results analyzed at the analysis-related department or the analysis-related business provider. Based on this, examinees can receive the feedback on the results of the analysis immediately.

EXAMPLE

Next, for preparing a calibration curve to be memorized by a memory unit of the measuring device of the present invention, influence from the addition of NaCl, KCl, and $CaCl_2$ to an antigen-antibody reaction system was examined by a measurement with the nephelometric immunoassay.

In the examination, influences in the case where each salt existed in the reaction solution in concentrations of 0 M, 0.050 M, 0.15 M, and 0.30 M were examined. For preparation of a buffer solution and the like in this Example, pure water filtered through Milli-Q SP TOC (manufactured by Millipore Corporation) was used. Also, for not particularly noted reagent such as salts and buffers, those manufactured by Wako Pure Chemical Industries, Ltd. were used, and for polyethylene glycol 6000 (PEG6000), the first-grade reagent was used, and for other reagents, a special-grade reagent was used.

Also, in this Example, for comparison, a human albumin measurement with an anti-human albumin polyclonal antibody was carried out. The anti-human albumin polyclonal antibody was refined from a rabbit antiserum immunized with human albumin with Protein A (manufactured by Amersham Pharmacia Biotech) column chromatography. For an equilibration buffer solution of the column, a mixture solution (pH8.9) including 1.5 M of glycin and 3.0 M of NaCl was used, and for an elution buffer solution, 0.1 M of citric acid (pH4.0) was used. Dialysis was carried out for the refined antibody several times with a buffer solution (pH7.4) including 0.05 M of 3-(N-Morpholino) propane sulfonic acid (MOPS), 0.15 M of NaCl, and 0.04% (w/v) of $NaN_3$, in 100-times volume, by using a dialysis tube with an amount of fraction molecule of ten thousand. The 0.15 M of NaCl in the dialysis buffer solution was added to prevent autoagglutination based on the antibody while in storage. The one with the replaced buffer solution by the dialysis was regarded as an anti-human albumin polyclonal antibody storage solution, and with an absorbance measurement with 280 nm, its concentration was estimated (3.2 mg/ml).

The human albumin (manufactured by Wako Pure Chemical Industries, Ltd.) as an antigen was dissolved in a buffer solution (pH7.4) including 0.05 M of MOPS and 0.04% of $NaN_3$, and 100 mg/dl of a solution for storage was prepared. The anti-human albumin polyclonal antibody solution and the storage solution for the human albumin were stored at 4° C. until usage. The pH adjustment for the following solutions is done by using NaOH.

For the buffer in this Example, MOPS was used. The MOPS was one of the Good buffers comprising various amine compounds, devised by Good et al. One of the characteristics includes dual polar ion buffer solution, and compared with ionic buffer solution, have less salt effects. Thus, this was used to further clarify the contrast in the results of this Example. The MOPS used was manufactured by Dojin Glocal Corporation.

For the buffer solution used to check the effects of each salt, two kinds were prepared as shown in below for respective salinity concentrations, one including PEG, and the other not including PEG.

For the buffer solution not including the added salt, 0.050 M of MOPS buffer solution (pH7.4) and a buffer solution (pH7.4) including 0.050 M of MOPS and 6% (w/v) of PEG6000 were prepared.

For the buffer solution including NaCl as the added salt, 0.050 M of MOPS buffer solution (pH7.4) including 0.050 M, 0.15 M, and 0.30 M of NaCl and a buffer solution (pH7.4) including 0.050 M of MOPS and 6% (w/v) of PEG6000 were prepared. For the buffer solution including KCl as an added salt, 0.050 M MOPS buffer solution (pH7.4) including 0.050 M, 0.15 M, and 0.30 M of KCl and a buffer solution (pH7.4) including 0.050 M MOPS and 6% (w/v) PEG6000 were prepared. For a buffer solution including $CaCl_2$ as an added salt, 0.050 M MOPS buffer solution (pH7.4) including 0.050 M, 0.15 M, and 0.30 M of $CaCl_2$, and a buffer solution (pH7.4) including 0.050 M MOPS and 6% (w/v) of PEG6000 were prepared.

For the measurement by the nephelometric immunoassay, a spectrofluorophotometer (RF-5300PC manufactured by Shimadzu Corporation) was used. A constant temperature cell holder (no. 206-15440 manufactured by Shimadzu Corporation) was placed in a sample room of the spectrofluorophotometer, and connected to a low-constant temperature tank (EL-15 manufactured by TIETECH Co., Ltd.). Water with its temperature kept to 25° C. was circulated to keep the measurement temperature constant.

For the measurement conditions of the spectrofluorophotometer, both the excitation wavelength and the fluorescent wavelength were set to 660 nm, and a bandwidth of the excitation side was set to 1.5 nm, and of the fluorescent was set to 3 nm, and the sensitivity was set to High.

Influences from each of the added salts were measured as in below. That is, measurements for the added salt concentrations of 0 M, 0.050 M, 0.15 M, and 0.30 M were considered as a set of measurement, and the case of the measurement with the concentration 0 M was considered a control in measured fluctuations depending upon measurement system on the measurements of influences from each added salt. For the measurement in the case where the concentration is 0 M, the buffer solution without the added salt as prepared in the above was used.

The anti-human albumin polyclonal antibody solution did not include the PEG as prepared in the above, and diluted to a concentration of 1.0 mg/ml with a buffer solution with matching added salt to be measured and its concentration. By using the same buffer solution, the human albumin storage solution was diluted to prepare respective human albumin solutions with concentrations of 0, 1, 5, 10, 50, and 100 mg/dl.

Preparation of the Reaction Liquid was Done as in Below. First, 2.0 ml of a buffer solution including PEG and matching added salt to be measured and a concentration, and 0.67 ml of a buffer solution not including PEG and matching added salt to be measured and a concentration were taken, and both were mixed by stirring.

Then, 0.3 ml of the anti-human albumin polyclonal antibody solution prepared in the above was added and mixed by stirring, and further, 0.03 ml of the human albumin solution as prepared in the above was added and mixed by stirring. The final concentrations of the anti-human albumin polyclonal antibody and the human albumin were, about 0.10 mg/ml for the anti-human albumin polyclonal antibody, and for the human albumin, the value of the concentration of the human albumin solution used for the reaction multiplied by 0.01. The final concentration of the PEG6000 was 4% (w/v).

Then, the above mixture was transferred to a quartz cell for the fluorescent analysis, and set in the spectrofluorophotometer. A T-thermocouple (no. 219-4696 manufactured by RS Components Ltd.) was immersed in the cell, and the cell was closed tight for preventing drying. From the point when two minutes were passed after mixing the human albumin, a measurement was carried out for 900 seconds with an interval of 0.08 second in a timecourse measurement. The temperature change in the cell while in measurement was monitored by connecting the T-thermocouple to a digital multithermometer (TR2114 manufactured by ADVANTEST CORPORATION). The measurement of the call blank value was carried out before the measurement for respective reaction with pure water, and the value was deducted from the measured value. An average value of the obtained scattered light intensity measurement value of 600 to 900 seconds was calculated and regarded as respective measurement value.

In FIGS. 15 to 17, values are plotted by deducting the average value in the case where human albumin was not included in corresponding salt and concentration from each average value. FIG. 15 shows the results when NaCl was added, FIG. 16 shows the results when KCl was added, and FIG. 17 shows the results when $CaCl_2$ was added.

As shown in FIGS. 15 to 17, the antigen-antibody reactions differ based on the salt concentrations. From these results, it is clear that different antigen-antibody reaction amounts may be shown based on the difference in salt concentration of the sample, even though the sample has the same concentration of the human albumin. From the results in the above, data showing relations between the antigen concentrations and the exit light intensity for each salt concentrations could be obtained for each salt. This is set as a calibration curve, and by using the salt concentration obtained by an electrochemical measurement, with correction of the exit light intensity measured by the optical measurement, the antigen concentration in the sample liquid can be obtained with higher precision.

INDUSTRIAL APPLICABILITY

Based on the present invention, with a sensor having a simple structure as noted in the above, an optical measurement and an electrochemical measurement of a sample can be done simultaneously, and a plurality of items can be measured quickly and accurately. Especially, although there is a problem in that usually a reagent used for the optical measurement gives adverse effects on an electrochemical measurement, based on the above structure, such problem can be solved. Further, based on the present invention, with the use of the sensor, a measuring device and a measuring method in which a plurality of items can be measured quickly and accurately can be realized.

Therefore, the present invention is useful in examinations in medical field and medical-related examination filed, especially in urinalysis.

The invention claimed is:

1. A measuring method for an analyte using a sensor comprising:

a sample-holding unit including a space for holding a sample including a first analyte comprising an antigen and a second analyte comprising an ion;

a sample-supplying port for supplying said sample to said sample-holding unit, the port being connected to the space;

a detecting unit for carrying out an electrochemical measurement, the detecting unit being provided in said sample-holding unit;

a light-entrance unit for introducing incident light to said sample-holding unit, the light-entrance unit being provided in said sample-holding unit;

a light-exit unit for releasing outgoing light from inside said sample-holding unit to outside said sample-holding unit, the light-exit unit being provided in said sample-holding unit; and a reagent-holding unit for holding a reagent comprising an antibody for said optical measurement, the reagent-holding unit being provided in said sample-holding unit;

wherein in a flowing direction of said sample supplied from said sample-supplying port in said sample-holding unit, said sample-supplying port, said detecting unit, and said reagent-holding unit are positioned in the order recited;

the method comprising the steps of:

(A) supplying said sample to said sample-holding unit;

(B) applying a voltage to said detecting unit;

(C) measuring an electric-signal from said detecting unit;

(D-1) quantifying said second analyte based on said electric-signal measured in said step (C);

(D-2) causing antigen-antibody reaction between said first analyte in said sample and said antibody held in said sample-holding unit;

(E) applying incident light to said sample held in said sample-holding unit via said light-entrance unit;

(F) measuring outgoing light released from inside said sample-holding unit to outside said sample-holding unit via said light-exit unit, caused by the application of said incident light; and (G) quantifying said first analyte based on said outgoing light measured in said step (F) and quanitification result of said second analyte.

2. The measuring method in accordance with claim 1, wherein upon detecting said electric-signal in said step (C), said incident light is applied in said step (E).

3. The measuring method in accordance with claim 1, wherein said detecting unit comprises an ion-selective electrode.

* * * * *

UNITED STATES PATENT AND TRADEMARK OFFICE
CERTIFICATE OF CORRECTION

PATENT NO. : 7,691,255 B2
APPLICATION NO. : 11/579638
DATED : April 6, 2010
INVENTOR(S) : Fumihisa Kitawaki et al.

It is certified that error appears in the above-identified patent and that said Letters Patent is hereby corrected as shown below:

On the title page,

In Item "(87) PCT Publ. No.:",
please delete "WO2005/188960", and add -- WO2005/108960 --.

Signed and Sealed this

Twenty-sixth Day of October, 2010

David J. Kappos
*Director of the United States Patent and Trademark Office*